(12) United States Patent
Coghlan et al.

(10) Patent No.: US 7,696,221 B2
(45) Date of Patent: Apr. 13, 2010

(54) THIENOISOQUINOLINE-PHENYL SULFONAMIDES AND THEIR USE AS ER-NFκB INHIBITORS

(75) Inventors: Richard Dale Coghlan, Phoenixville, PA (US); William Floyd Fobare, Lawrenceville, NJ (US); Eugene John Trybulski, Huntingdon Valley, PA (US)

(73) Assignee: Wyeth LLC, Madison, NJ (US)

( * ) Notice: Subject to any disclaimer, the term of this patent is extended or adjusted under 35 U.S.C. 154(b) by 1140 days.

(21) Appl. No.: 11/313,140

(22) Filed: Dec. 20, 2005

(65) Prior Publication Data

US 2006/0154875 A1 Jul. 13, 2006

Related U.S. Application Data

(60) Provisional application No. 60/638,206, filed on Dec. 21, 2004.

(51) Int. Cl.
C07D 409/04 (2006.01)
C07D 413/04 (2006.01)
A61K 31/4365 (2006.01)

(52) U.S. Cl. ........................ 514/290; 546/80
(58) Field of Classification Search .................. None
See application file for complete search history.

(56) References Cited

FOREIGN PATENT DOCUMENTS

| EP | 0 446 604 A2 | 9/1991 |
|---|---|---|
| WO | 2004/009582 A1 | 1/2004 |
| WO | 2004/058772 A1 | 7/2004 |

OTHER PUBLICATIONS

Dorwald F. A. Side Reactions in Organic Synthesis, 2005, Wiley: VCH, Weinheim p. IX of Preface.*
Adams, M. R. et al., "Inhibition of Coronary Artery Atherosclerosis by 17-beta Estradiol in Ovariectomized Monkeys," *Arterio.*, 1990, 10(6),1051-1057.
Alexander et. al., "Initiation of Hormone Replacement Therapy After Acute Myocardial Infarction Is Associated With More Cardiac Events During Follow-Up," *J. Am. Coll. Cardio.*, 2001, 38, 1-7.
Bauer M. A., Herrmann F., "Interleukin-6 in clinical medicine,"*Ann. Hematol.*, 1991, 62, 203-210.
Brunnett, E. W., et al., "Heterocyclic Amines V. Electrophilic Substitution in Some Carbamate Derivatives of 3-Aminothiophene," *J Pharm. Sci.*, 1968, 57(11), 2003-2005.
Brunnett, E. W., et al., "Heterocyclic Amines. IV. Urethan and Urea Derivatives of 3-Aminothiophene (1),"*J. Heterocycl. Chem.*, 1968, 5, 417-418.
Cefalu, W., "The Use of Hormone Replacement Therapy in Postmenopausal Women with Type 2 Diabetes," *J Womens Health & Gender-based Med.*, 2001, 10(3), 241-255.
Cercek, B. et al., "Nuclear factor-κB Activity and arterial response to balloon injury," *Atherosclerosis 131*, 59-66 (1997).

Chandrasekar, B. et al. "Ischemia-Reperfusion of Rat Myocardium Activates Nuclear Factor- κB and Induces Neutrophil Infiltration Via Lipopolysaccharide-Induced CXC Chemokine," *Circulation*, 2001 103, 2296-2302.
Cuzzocrea, S. et al., "17β-Estradiol Antiinflammatory Activity in Carrageenan-Induced Pleurisy," *Endocrinology*, 2000, 141, 1455-1463.
Delyani, J. A. et al., "Protection from Myocardial Reperfusion Injury by Acute Administration of 17 β-Estradiol," *J. Molec. Cell. Cardiol.*, 1996, 28, 1001-1008.
Dietrich, H. et al., "Mouse Model of Transplant Arteriosclerosis," *Arterioscler. Thromb. Vasc. Biol.*, 2000, 20, 343-352.
Dubal, D. B. et al., "Estradiol Modulates bcl-2 in Cerebral Ischemia: A Potential Role for Estrogen Receptors," *J. Neurosci.*, 1999, 19, 6385-6393.
Dubal, D. B. et al., "Estrogen receptor α, not β, is a critical link in estradiol-mediated protection against brain injury," PNAS, USA, 2001, 98, 1952-1957.
Felson, D. T. et al., "The effects of estrogen on osteoarthritis," *Curr Opinion Rheum*, 1998, 10, 269-272.
Grodstein F. et. al., "Postmenopausal Hormone Use and Secondary Prevention of Coronary Events in the Nurses' Health Study,"*Ann. Int. Med*, 2001, 135, 1-8.
Grodstein, F. et. al., "A Prospective, Observational Study of Postmenopausal Hormone Therapy and Primary Prevention of Cardiovascular Disease," *Ann. Int. Med.*, 2000, 133, 933-41.
Hulley, S. et. al., "Randomized Trial of Estrogen Plus Progestin for Secondary Prevention of Coronary Heart Disease in Postmenopausal Women," *J. Am. Med. Assoc.*, 1998, 280, 605-13.
Izumi, T. et al., "Blockade of the natriuretic peptide receptor guanylyl cyclase-A inhibits NF-κB activation and alleviates myocardial ischemia/reperfusion injury," *J. Clin. Invest.*, 2001, 108, 203-213.
Kadokami, T. et al., "Anti-Tumor Necrosis Factor-α Antibody Limits Heart Failure In a Transgenic Model," *Circulation*, 2001, 104, 1094-1097.
Karas, R. H. et al., "Effects of Estrogen on the Vascular Injury Response in Estrogen Receptor α,β (Double) Knockout Mice," *Circ. Res.*, 2001, 89, 534-539.

(Continued)

*Primary Examiner*—Rita J Desai
(74) *Attorney, Agent, or Firm*—Pepper Hamilton LLP

(57) ABSTRACT

This invention provides estrogen receptor modulators having the structure:

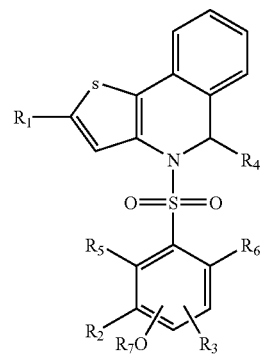

wherein $R_1$ to $R_7$ are as defined in the specification; or a pharmaceutically acceptable salt thereof.

12 Claims, No Drawings

OTHER PUBLICATIONS

Kurebayashi S. et. al., "Characterization of Mechanisms of Interleukin-6 Gene Repression by Estrogen Receptor," *J. Steroid Biochem. Molec. Biol.*, 1997, 60, 11-17.

Lin, C. C. et.al., "Pulmonary function changes and increased Th-2 cytokine expression and nuclear factor kB activation in the lung after sensitization and allergen challenge in brown Norway rats," *Immunol. Lett.*, 2000, 73, 57-64.

Lou, H. et al., "Inhibition of Transplant Coronary Arteriosclerosis in Rabbits by Chronic Estradiol Treatment Is Associated With Abolition of MHC Class II Antigen Expression," *Circulation*, 1996, 94, 3355-3361.

Lundeen, S. G. et al., "Rat uterine complement C3 expression as a model for progesterone receptor modulators: characterization of the new progestin trimegestone," *J. Steroid Biochem Biol.*, 2001, 78, 137-143.

Mankin, H. J. et al., "Biochemical and Metabolic Abnormalities in Articular Cartilage from Osteo-Arthritic Human Hips," *Journal of Bone & Joint Surgery*—American vol. 53, 523-537 (1971).

Merchenthaler, I. et al., "The effect of estrogens and antiestrogens in a rat model for hot flush," *Maturitas*, 1998, 30, 307-316.

Nathan, L. et. al., "Estradiol Inhibits Leukocyte Adhesion and Transendothelial Migration in Rabbits in Vivo," *Circ. Res.*, 1999, 85, 377-385.

Pelletier et al., "Osteoarthritis, an Inflammatory Disease," *Arthr. & Rheum.*, 2001, 44, 1237-1247.

Poole, A. R et al., "Rheumatoid-Like Joint Lesions in Rabbits Injected Intravenously with Bovine Serum," *International Archives of Allergy & Applied Inmunology*, 1977, 54,97-113.

Prokai, L. et al., "Synthesis and Biological Evaluation of 17β-Alkoxyestra-1,3,5(10)-trienes as Potential Neuroprotectants Against Oxidative Stress," *J. Med. Chem.*, 2001, 44, 110-114.

Reis et. al., "Estrogen Is Associated With Improved Survival in Aging Women With Congestive Heart Failure: Analysis of the Vesnarinone Studies," *J. Am. Coll. Cardio.*, 2000, 36, 529-33.

Roth, A. et. al., "Phytoestrogen Kaempferol (3,4',5,7-Tetrahydroxylflavone) Protects PC12 and T47D Cells From β-Amyloid-Induced Toxicity," *J. Neurosci. Res.*, 1999, 57, 399-404.

Schonknecht, P. et. al., "Reduced cerebrospinal fluid estradiol levels are associated with increased β-amyloid levels in female patients with Alzheimer's disease," *Neurosci. Lett.*, 2001, 307, 122-124.

Shughrue, P. J. et al., "Regulation of Progesterone Receptor Messenger Ribonucleic Acid in the Rat Medial Preoptic Nucleus by Estrogenic and Antiestrogenic Compounds: An in Situ Hybridization Study," *Endocrinology*, 1997, 138, 5476-5484.

Smirnoff, P. et al., "The Protective Effect of Estrogen Against Chemically Induced Murine Colon Carcinogenesis Is Associated With Decreased CpG Island Methylation and Increased mRNA and Protein Expression of the Colonic Vitamin D Receptor," *Oncology Research*, 1999, 11, 255-264.

Stetson, S. J. et al., "Cardiac Hypertrophy After Transplantation Is Associated With Persistent Expression of Tumor Necrosis Factor-α," *Circulation*, 2001, 104, 676-681.

Sullivan, T. R. et al. "Estrogen Inhibits the Response-to-Injury in a Mouse Carotid Artery Model," *J. Clin. Invst.*, 1995, 96, 2482-8.

Yagi, K., "Short Communications. A Simple Fluorometric Assay for Lipoperoxide in Blood Plasma," *Biochemical Medicine*, 1976, 15, 212-216.

Yang, Y., et al., "The First Synthesis of Thieno[c]isoquinolines and an Improved Synthesis of Phenanthridine and Thieno[c]isoquinolines through Pd(0) catalyzed Coupling of *ortho*-Formylarylboronic Acids with Functionalized Aryl Halides," *J. Heterocycl. Chem.*, 1989, 26, 865-868.

Yokoseki, O. et al., "*cis* Element Decoy Against Nuclear Factor- κB Attenuates Development of Experimental Autoimmune Myocarditis in Rats," *Circ. Res.*, 2001, 89, 899-906.

Yuan et al., "Reversal of Obesity- and Diet-Induced Insulin Resistance with Salicylates or Targeted Disruption of *Ikk*β," *Science*, 2001, 293, 1673-1677.

Zaulyanov, L. L. et al., "Glutamate Receptor Requirement for Neuronal Death from Anoxia-Reoxygenation: An in Vitro Model for Assessment of the Neuroprotective Effects of Estrogens," *Cellular & Molecular Neurobiology*, 1999, 19, 705-718.

\* cited by examiner

THIENOISOQUINOLINE-PHENYL SULFONAMIDES AND THEIR USE AS ER-NFκB INHIBITORS

RELATED APPLICATIONS

The present application claims benefit to U.S. Provisional Application Ser. No. 60/638,206 filed Dec. 21, 2004, which is incorporated herein by reference in its entirety.

FIELD OF THE INVENTION

This invention relates to thienoisoquinoline-phenylsulfonamide compounds, compositions containing them, their use as ER-NF$_k$B inhibitors, and methods of their preparation.

BACKGROUND OF THE INVENTION

The ability of ligands for the estrogen receptor to inhibit inflammatory gene expression (causing a reduction of cytokines, chemokines, adhesion molecules and inflammatory enzymes) is believed to provide a means to treat the inflammatory component of diseases such as atherosclerosis, myocardial infarction (MI), congestive heart failure (CHF), inflammatory bowel disease and arthritis. Other potential therapeutic indications for these type of molecules include type II diabetes (Cefalu, *J Womens Health & Gender-based Med.* 2001, 10, 241 & Yuan et al., *Science,* 2001, 293, 1673), osteoarthritis (Pelletier et al., *Arthr. & Rheum.,* 2001, 44:1237 and Felson et al. *Curr Opinion Rheum,* 1998, 10, 269) asthma (Chin-Chi Lin et. al., *Immunol. Lett.,* 2000, 73, 57), Alzheiemer's disease (Roth, A. et. al., *J. Neurosci. Res.,* 1999, 57, 399) and autoimmune diseases such as multiple sclerosis and rheumatoid arthritis.

A common component of these chronic inflammatory conditions is suspected to be polymorphonuclear leukocyte and monocyte infiltration into the site of damage through increased expression of cytokines and adhesion molecules responsible for their recruitment. Overproduction of the cytokine interleukin (IL-6) has been associated with states of chronic inflammation (Bauer M. A., Herrmann F., *Ann. Hematol.,* 1991, 62, 203). Synthesis of the IL-6 gene is induced by the transcription factor nuclear factor κB (NF-κB). Interference at this step in the inflammatory process can effectively regulate the uncontrolled proliferative process that occurs in these chronic conditions.

In endothelial cells, 17β-estradiol (E2) inhibits IL-1β induced NF-κB reporter activity and IL-6 expression in an ER dependent fashion (Kurebayashi S. et. al., *J. Steroid Biochem. Molec. Biol.,* 1997, 60, 11). This has been said to correlate with anti-inflammatory action of E2 in vivo as confirmed in different animal models of inflammation. In models of atherosclerosis, E2 was shown to protect endothelial cell integrity and function and to reduce leukocyte adhesion and intimal accumulation (Adams, M. R. et al., *Arterio.,* 1990, 1051, Sullivan, T. R. et al. *J. Clin. Invst.* 1995, 96, 2482, Nathan, L. et. al., *Circ. Res.,* 1999, 85, 377). Similar effects of estrogen on the vascular wall have also been demonstrated in animal models of myocardial infarction (Delyani, J. A. et al., *J. Molec. Cell. Cardiol.,* 1996, 28, 1001) and congestive heart failure. Clinically, estrogen replacement therapy (ERT) has been demonstrated to reduce the risk of mortality in patients with both CHF (Reis et. al., *J. Am. Coll. Cardio.,* 2000, 36, 529) and MI (Grodstein, F. et. al., *Ann. Int. Med.,* 2000, 133, 933, Alexander et. al., *J. Am. Coll. Cardio.,* 2001, 38, 1 and Grodstein F. et. al., *Ann. Int. Med,* 2001, 135,1). In ERT, clinical studies demonstrated an influence of E2 on the decrease in the production of β-amyloid 1-42 (Aβ42), a peptide central for the formation of senile plaques in Alzheimer's disease (Schonknecht, P. et. al., *Neurosci. Lett.,* 2001, 307, 122).

17-β-estradiol, however, also strongly stimulates creatine kinase expression. Thus, in ERT some potential unwanted side effects, such as an increase risk of cardiovascular events in the first year of use, have been demonstrated (Hulley, S. et. al., *J. Am. Med. Assoc.,* 1998, 280, 605) as well as proliferative effects on uterine and breast tissue.

SUMMARY OF THE INVENTION

The instant invention relates to compounds that are able to serve as ligands for the estrogen receptor. Preferred compounds are thienoisoquinoline-phenylsulfonamide compounds. In certain preferred embodiments, such compounds are of the formula:

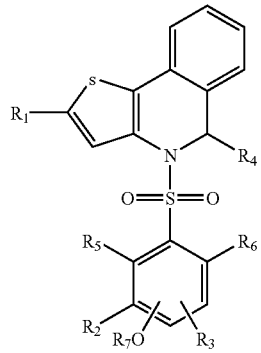

where $R_1$ is hydrogen, alkyl, halogen, aryl, or heteroaryl; $R_2$, $R_3$, $R_5$, and $R_6$ are, independently, hydrogen, hydroxy, lower alkyl, alkoxy, or halogen; $R_4$ is alkyl; and $R_7$ is hydrogen, —(C=O)$R_{16}$, —S(O)$_2R_{17}$, —S(O)$_2$N($R_{18}$)($R_{19}$), or D-glucuronidate, $R_{16}$ is alkyl, aralkyl or aryl, $R_{17}$ is alkyl, aryl, heteroaryl, cycloalkyl, alkenyl, cycloalkenyl, or alkynyl, $R_{18}$ and $R_{19}$ are, independently, hydrogen, alkyl, alkenyl, alkynyl, cycloalkyl, monofluoroalkyl, perfluoroalkyl, aryl, arylalkyl, cycloalkenyl, heteroaryl, heteroarylalkyl, hydroxy-($C_2$-$C_6$)alkyl, alkoxyalkyl, alkylthioalkyl, carbonyl, acyl, alkoxycarbonyl, —C(O)NH$_2$, alkylaminocarbonyl, dialkylaminocarbonyl, alkylaminoalkyl, or dialkylaminoalkyl, or $R_{18}$ and $R_{19}$ are taken together with the nitrogen atom to which they are attached to form a saturated, unsaturated or partially saturated $C_4$-$C_6$ carbon ring.

In certain embodiments, $R_5$ and $R_6$ are H.

In some embodiments, the compound is of the formula:

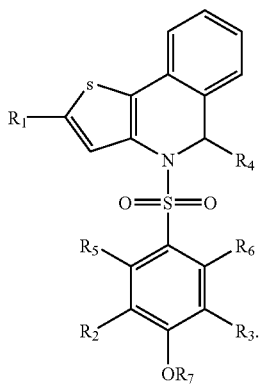

In some preferred embodiments, $R_1$ is methyl, ethyl, halogen, phenyl, or heteroaryl. In other preferred embodiments, $R_1$ is methyl, ethyl, bromo, phenyl, or thienyl. In certain compositions of the invention, $R_2$ is H or Br. In other compositions, $R_3$ is H or Br. $R_2$ and $R_3$ are each, independently, H or Br in yet other preferred compositions.

In certain preferred embodiments, $R_4$ is methyl or ethyl. In other preferred embodiments, $R_7$ is H or methyl.

In another aspect, the invention is drawn to pharmaceutical compositions that comprise one or more compounds of the invention and a pharmaceutically acceptable carrier.

In yet other aspects, the invention concerns methods of treating or inhibiting chronic inflammatory disease in a mammal in need thereof, which comprise administering to said mammal an effective amount of a compound of the invention.

Such diseases include rheumatoid arthritis, spondyloarthropathies, osteoarthritis, psoriatic arthritis, juvenile arthritis, inflammatory bowel disease, Crohn's disease, ulcerative colitis, indeterminate colitis, psoriasis, asthma and chronic obstructive pulmonary disease.

The invention is also directed to methods of treating or inhibiting stroke, ischemia, or reperfusion injury in a mammal in need thereof, which comprise administering to said mammal an effective amount of a compound of the invention. In other embodiments, the invention concerns methods of lowering cholesterol, triglycerides, Lp(a), and LDL levels; inhibiting or treating hypercholesteremia, hyperlipidemia, cardiovascular disease, atherosclerosis, acute coronary syndrome, peripheral vascular disease, restenosis, or vasospasm in a mammal.

In yet other aspects, the compounds of the invention can be used for treating or inhibiting Alzheimer's disease, cognitive decline, senile dementia, or type II diabetes in a mammal.

DETAILED DESCRIPTION OF THE INVENTION

Preferred compounds of the present invention are those that block interleukin-1β (IL-1β) induced nuclear factor κB (NF-κB) luciferase reporter activity or interleukin-6 (IL-6) expression in an ER dependent fashion in human endothelial cells. Compounds useful in the instant invention show preferably little or no proliferative effects on uterine and breast tissue that is associated with estrogen in vivo. A lack of estrogen side effects can be confirmed in vitro by the lack of expression of creatine kinase (CK), a classic estrogen responsive gene. The compounds described herein are expected to prove useful for the treatment and prevention of chronic inflammatory diseases without stimulating uterine and breast cell proliferation as found with classic estrogens.

Compounds of the present invention include thienoisoquinoline-phenylsulfonamide compounds. In some aspects, the compounds may be represented by the formula I as shown above.

In certain embodiments, $OR_7$ is in the position para to the sulfonyl group. In some embodiments, $OR_7$ is meta to the sulfonyl group.

The instant invention is illustrated by the following compounds:

4-[(5-Methylthieno[3,2-c]isoquinolin4(5H)-yl)sulfonyl]phenol,

4-[(5-Ethylthieno[3,2-c]isoquinolin-4(5H)-yl)sulfonyl]phenol,

4-[(2-Bromo-5-methylthieno[3,2-c]isoquinolin-4(5H)-yl)sulfonyl]phenol,

4-{[(5R)-2-bromo-5-methylthieno[3,2-c]isoquinolin-4-(5H)-yl]sulfonyl}phenol,

4-{[(5S)-2-bromo-5-methylthieno[3,2-c]isoquinolin-4-(5H)-yl]sulfonyl}phenol,

4-[(2-Bromo-5-ethylthieno[3,2-c]isoquinolin-4(5H)-yl)sulfonyl]phenol,

4-[(5-Ethyl-2-thien-3-ylthieno[3,2-c]isoquinolin-4(5H)-yl)sulfonyl]phenol,

4-[(5-Ethyl-2-phenylthieno[3,2-c]isoquinolin-4(5H)-yl)sulfonyl]phenol,

2-Bromo-4-[(2-bromo-5-methylthieno[3,2-c]isoquinolin-4(5H)-yl)sulfonyl]phenol, 2,6-Dibromo-4-[(2-bromo-5-methylthieno[3,2-c]isoquinolin-4(5H)-yl)sulfonyl]phenol. and 4-[(2,5-Diethylthieno[3,2-c]isoquinolin-4(5H)-yl)sulfonyl]phenol.

DESCRIPTION OF CHEMICAL GROUPS

The term "alkyl", employed alone, is defined herein as, unless otherwise stated a $C_1$-$C_{20}$ monovalent saturated hydrocarbon moiety, eg. either a ($C_1$-$C_{20}$) straight chain or ($C_3$-$C_{20}$) branched-chain. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, n-heptyl, n-octyl, and the like. It is preferred that straight chain alkyl moieties have 1-6 carbon atoms, and branched alkyl moieties have 3-8 carbon atoms.

The term "alkenyl", employed alone, is defined herein as, unless otherwise stated, a $C_2$-$C_{20}$ monovalent hydrocarbon moiety containing at least one double bond, e.g either a ($C_2$-$C_{20}$) straight chain or ($C_3$-$C_{20}$) branched-chain, Such hydrocarbon alkenyl moieties may be mono or polyunsaturated, and may exist in the E or Z configurations. The compounds of this invention are meant to include all possible E and Z configurations. Examples of mono or polyunsaturated hydrocarbon alkenyl moieties include, but are not limited to, chemical groups such as vinyl, 2-propenyl, isopropenyl, crotyl, 2-isopentenyl, butadienyl, 2-(butadienyl), 2,4-pentadienyl, 3-(1,4-pentadienyl), and higher homologs, isomers, and the like. It is preferred that straight chain alkenyl moieties have 2-7 carbon atoms, and branched alkenyl moieties have 3-8 carbon atoms.

The term "alkynyl", employed alone, is defined herein as, unless otherwise stated, a $C_1$-$C_{20}$ monovalent saturated hydrocarbon moiety, containing at least one triple bond, eg either a ($C_2$-$C_{20}$) straight chain or ($C_3$-$C_{20}$) branched-chain. Examples of alkynyl moieties include, but are not limited to, chemical groups such as ethynyl, 1-propynyl, 1-(2-propynyl), 3-butynyl, and higher homologs, isomers, and the like. It is preferred that straight chain alkynyl moieties have 2-7 carbon atoms, and branched alkynyl moieties have 3-8 carbon atoms.

The term "alkylene" , employed alone or in combination with other terms, is defined herein as, unless otherwise stated, either a ($C_1$-$C_{20}$) straight chain or ($C_2$-$C_{20}$) branched-chain bivalent hydrocarbon moiety derived from an alkane; or a ($C_2$-$C_{20}$) straight chain or branched-chain bivalent hydrocarbon moiety derived from an alkene. Such hydrocarbon alkylene moieties may be fully saturated, or mono or polyunsaturated, and may exist in the E or Z configurations. The compounds of this invention are meant to include all possible E and Z configurations. Examples of saturated and unsaturated hydrocarbon alkylene moieties include, but are not limited to bivalent chemical groups such as —$CH_2$—, —$CH_2CH_2$—, —$CH_2CH_2CH_2$—, —$CH_2CH_2CH_2CH_2$—, —CH=CH—, —CH=CHCH=CH—, vinylidene, and higher homologs, isomers, and the like. Preferred alkylene chains have 2-7 carbon atoms.

The term "cycloalkyl", employed alone or in combination with other terms, is defined herein as, unless otherwise stated, a monocyclic, bicyclic, tricyclic, fused, bridged, or spiro monovalent saturated hydrocarbon moiety of 3-10 carbon atoms, wherein the carbon atoms are located inside or outside of the ring system. Any suitable ring position of the cycloalkyl moiety may be covalently linked to the defined chemical structure. Examples of $C_3$-$C_{10}$ cycloalkyl moieties include, but are not limited to, chemical groups such as cyclopropyl, cyclopropylmethyl, cyclobutyl, cyclopentyl, cyclohexyl, cyclohexylmethyl, cyclohexylethyl, cycloheptyl, norbornyl, adamantyl, spiro[4.5]decanyl, and homologs, isomers, and the like.

The term "cycloalkenyl", employed alone or in combination with other terms, is defined herein as, unless otherwise stated, a monocyclic, bicyclic, tricyclic, fused, bridged, or spiro monovalent unsaturated hydrocarbon moiety of 3-10 carbon atoms containing at least one double bond, wherein the carbon atoms are located inside or outside of the ring system. Any suitable ring position of the cycloalkenyl moiety may be covalently linked to the defined chemical structure. Examples of $C_3$-$C_{10}$ cycloalkenyl moieties include, but are not limited to, chemical groups such as cyclopropenyl, cyclopropenylmethyl cyclobutenyl, cyclopentenyl, cyclohexenyl, cyclohexenylmethyl, cyclohexenylethyl, cycloheptenyl, norbornenyl, and homologs, isomers, and the like.

The term "cycloalkylene", employed alone, is defined herein as, unless otherwise stated, a bivalent moiety of 3-10 carbon atoms derived from a monocyclic, bicyclic, tricyclic, fused, bridged, or spiro hydrocarbon. Such hydrocarbon cycloalkylene moieties may be fully saturated, or mono or polyunsaturated, and may exist in the E or Z configurations. The compounds of this invention are meant to include all possible E and Z configurations Any suitable ring position of the cycloalkylene moiety may be covalently linked to the defined chemical structure. Examples of saturated and unsaturated hydrocarbon cycloalkylene moieties include, but are not limited to, bivalent chemical groups such as cyclopropylene, cyclopentylene, cyclohexylene, cyclohexenylene, trans-decahydronaphthalenylene. spiro[3.3]heptenylene, and higher homologs, isomers, and the like.

The terms "halo" or "halogen", employed alone or in combination with other terms, is defined herein as, unless otherwise stated, a fluorine, chlorine, bromine, or iodine atom.

The term "monofluoroalkyl", employed alone, is defined herein as, unless otherwise stated, a $C_1$-$C_{10}$ monovalent saturated hydrocarbon moiety containing only one fluorine atom, eg either a ($C_1$-$C_{10}$) straight chain or ($C_3$-$C_{10}$) branched-chain. Examples of monofluoroalkyl moieties include, but are not limited to, chemical groups such as —CH$_2$F, —CH$_2$CH$_2$F, —CH(CH$_3$)CH$_2$CH$_2$F, and higher homologs, isomers, and the like. Preferred chain lengths are from 1-6 carbon atoms for straight chains and from 3-8 carbon atoms for branched chains.

The term "monofluoroalkenyl", employed alone, is defined herein as, unless otherwise stated, a $C_2$-$C_{10}$ monovalent unsaturated hydrocarbon moiety containing only one fluorine atom and at least one double bond, eg either a ($C_2$-$C_{10}$) straight chain or ($C_3$-$C_{10}$) branched-chain. Examples of monofluoroalkenyl moieties include, but are not limited to, chemical groups such as —CH=CH$_2$F, —CH$_2$CH=CH$_2$F, —CH=CHCH$_2$F, —C(CH$_3$)=CHF and higher homologs, isomers, and the like. Preferred chain lengths are from 2-7 carbon atoms for straight chains and from 3-8 carbon atoms for branched chains.

The term "perfluoroalkyl", employed alone or in combination with other terms, is defined herein as, unless otherwise stated, a $C_1$-$C_{10}$ monovalent saturated hydrocarbon moiety, containing two or more fluorine atoms eg, either a ($C_1$-$C_{10}$) straight chain or ($C_3$-$C_{10}$) branched-chain. Examples of perfluoroalkyl moieties include, but are not limited to, chemical groups such as trifluoromethyl, —CH$_2$CF$_3$, —CF$_2$CF$_3$, and —CH(CF$_3$)$_2$, and homologs, isomers, and the like. Preferred chain lengths are from 1-7 carbon atoms for straight chains and from 3-8 carbon atoms for branched chains.

The term "aryl", employed alone or in combination with other terms, is defined herein as, unless otherwise stated, an aromatic carbocyclic moiety of up to 20 carbon atoms, (eg 6-20 carbon atoms), which may be a single ring (monocyclic) or multiple rings (bicyclic, up to three rings) fused together or linked covalently. Any suitable ring position of the aryl moiety may be covalently linked to the defined chemical structure. Examples of aryl moieties include, but are not limited to, chemical groups such as phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like. It is preferred that the aryl moiety contain 6-14 carbon atoms.

The term "arylalkyl", employed alone or in combination with other terms, is defined herein as, unless otherwise stated, an aryl group, as herein before defined, eg $C_6$-$C_{20}$ arylsuitably substituted on any open ring position with an alkyl moiety wherein the alkyl chain is either a ($C_{1-7}$) straight or ($C_2$-$C_7$) branched-chain saturated hydrocarbon moiety. Examples of aryl($C_1$-$C_7$)alkyl moieties include, but are not limited to, chemical groups such as benzyl, 1-phenylethyl, 2-phenylethyl, diphenylmethyl, 3-phenylpropyl, 2-phenylpropyl, fluorenylmethyl, and homologs, isomers, and the like.

The term "heteroaryl", employed alone or in combination with other terms, is defined herein as, unless otherwise stated, an aromatic heterocyclic ring system, which may be a single ring (monocyclic) or multiple rings (bicyclic, up to three rings) fused together or linked covalently and having for example five to twenty ring atoms. The rings may contain from one to four hetero atoms selected from nitrogen (N), oxygen (O), or sulfur (S), wherein the nitrogen or sulfur atom(s) are optionally oxidized, or the nitrogen atom(s) are optionally substituted or quarternized. Any suitable ring position of the heteroaryl moiety may be covalently linked to the defined chemical structure. Examples of heteroaryl moieties include, but are not limited to, heterocycles such as furan, thiophene, pyrrole, N-methylpyrrole, pyrazole, N-methylpyrazole, imidazole, N-methylimidazole, oxazole, isoxazole, thiazole, isothiazole, 1H-tetrazole, 1-methyltetrazole, 1,3,4-oxadiazole, 1H-1,2,4-triazole, 1-methyl-1,2,4-triazole, 1,3,4-triazole, 1-methyl-1,3,4-triazole, pyridine, pyrimidine, pyrazine, pyridazine, benzoxazole, benzisoxazole, benzothiazole, benzofuran, benzothiophene, thianthrene, dibenzo[b,d]furan, dibenzo[b,d]thiophene, benzimidazole, N-methylbenzimidazole, indole, indazole, quinoline, isoquinoline, quinazoline, quinoxaline, purine, pteridine, 9H-carbazole, β-carboline, and the like.

The term "heteroarylalkyl", employed alone or in combination with other terms, is defined herein as, unless otherwise stated, a heteroaryl group, as before defined, suitably substituted on any open ring position with a $C_1$-$C_7$ alkyl moiety, eg wherein the alkyl chain is either a ($C_1$-$C_6$) straight or ($C_2$-$C_7$) branched-chain saturated hydrocarbon moiety. Examples of heteroarylalkyl moieties include, but are not limited to, chemical groups such as furanylmethyl, thienylethyl, indolylmethyl, and the like.

Heteroaryl chemical groups, as herein before defined, also include saturated or partially saturated heterocyclic rings. Examples of saturated or partially saturated heteroaryl moieties include, but are not limited to, chemical groups having 4-20 ring atoms such as azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydro-1,4-dioxanyl, tetrahydrofuranyl, tetrahydrothienyl, tetrahydroquinolinyl, tetrahydroisoquinolinyl, and the like.

The term "acyl", employed alone or in combination with other terms, is defined herein as, unless otherwise stated, either an alkyl, arylalkyl, heteroarylalkyl, ($C_2$-$C_{10}$) straight chain, or ($C_4$-$C_{11}$) branched-chain monovalent hydrocarbon moiety; wherein the carbon atom, covalently linked to the defined chemical structure, is oxidized to the carbonyl oxidation state. Such hydrocarbon moieties may be mono or poly-unsaturated, and may exist in the E or Z configurations. The compounds of this invention are meant to include all possible E and Z configurations. Examples of $C_2$-$C_{11}$ acyl moieties include, but are not limited to, chemical groups such as acetyl, propionyl, butyryl, 3,3-dimethylbutyryl, trifluoroacetyl, pivaloyl, hexanoyl, hexenoyl, decanoyl, benzoyl, nicotinyl, isonicotinyl, and homologs, isomers, and the like.

The term "hydroxyalkyl", employed alone or in combination with other terms, is defined herein as, unless otherwise stated, a ($C_1$-$C_{10}$) straight chain hydrocarbon, terminally substituted with a hydroxyl group. Examples of hydroxyalkyl moieties include chemical groups such as —$CH_2OH$, —$CH_2CH_2OH$, —$CH_2CH_2CH_2OH$, and higher homologs.

The term "alkoxy", employed alone or in combination with other terms is defined herein as, unless otherwise stated, either a ($C_1$-$C_{10}$) straight chain or ($C_3$-$C_{10}$) branched-chain hydrocarbon covalently bonded to an oxygen atom. Examples of $C_2$-$C_{10}$ alkoxy moieties include, but are not limited to, chemical groups such as methoxy, ethoxy, isopropoxy, sec-butoxy, tert-butoxy, decanoxy, and homologs, isomers, and the like.

The terms "aryloxy" or "heteroaryloxy", employed alone or in combination with other terms, or unless otherwise stated, are aryl or heteroaryl groups, as herein before defined, which are further covalently bonded to an oxygen atom. Examples of aryloxy, or heteroaryloxy moieties include, but are not limited to, chemical groups such as $C_6H_5O$—, 4-pyridyl-O—, and homologs, isomers, and the like.

The term "carbonyl", employed alone or in combination with other terms, is defined herein as, unless otherwise stated, a bivalent one-carbon moiety further bonded to an oxygen atom with a double bond. An example is

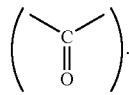

The term "alkoxycarbonyl", employed alone or in combination with other terms, is defined herein as, unless otherwise stated, an alkoxy group, as herein before defined, which is further bonded to a carbonyl group to form an ester moiety. Examples of alkoxycarbonyl moieties include, but are not limited to, chemical groups such as methoxycarbonyl, ethoxycarbonyl, isopropoxycarbonyl, sec-butoxycarbonyl, tert-butoxycarbonyl, decanoxycarbonyl, and homologs, isomers, and the like.

The term "alkylthio", employed alone or in combination with other terms, is defined herein as, unless otherwise stated, an alkyl group as previously defined covalently bonded to a sulfur atom. Examples of ($C_1$-$C_{10}$)alkylthio moieties include, but are not limited to, chemical groups such as methylthio, ethylthio, isopropylthio, sec-butylthio, tert-butylthio, decanylthio, and homologs, isomers, and the like. It is preferred that straight chain alkylthio moieties have 1-6 carbon atoms, and branched alkylthio moieties have 3-8 carbon atoms.

The terms "arylthio" or "heteroarylthio", employed alone or in combination with other terms, or unless otherwise stated, are aryl or heteroaryl groups, as herein before defined, which are further covalently bonded to a sulfur atom. Examples of arylthio or heteroarylthio moieties include, but are not limited to, chemical groups such as $C_6H_5S$—, 4-pyridyl-S—, and homologs, isomers, and the like.

The terms "alkoxyalkyl" or "alkylthioalkyl", employed alone or in combination with other terms, are an alkoxy or alkylthio group, as herein before defined, which is further covalently bonded to an unsubstituted ($C_1$-$C_{10}$) straight chain or unsubstituted ($C_2$-$C_{10}$) branched-chain hydrocarbon. Examples of alkoxyalkyl or alkylthioalkyl moieties include, but are not limited to, chemical groups such as, methoxymethyl, methylthioethyl, ethylthioethyl, isopropylthiomethyl, sec-butylthioethyl, —$CH_2CH(CH_3)OCH_2CH_3$ and homologs, isomers, and the like. It is preferred that straight chain alkoxyalkyl or alkylthioalkyl moieties have 1-6 carbon atoms, and branched alkoxyalkyl or alkylthioalkyl moieties have 3-8 carbon atoms.

The terms "aryloxyalkyl", "heteroaryloxyalkyl", "arylthioalkyl", or "heteroarylthioalkyl", employed alone or in combination with other terms, or unless otherwise stated, are aryloxy, heteroaryloxy, arylthio, or heteroarylthio groups, as herein before defined, which are further covalently bonded to an unsubstituted ($C_1$-$C_{10}$) straight chain or unsubstituted ($C_2$-$C_{10}$) branched-chain hydrocarbon. Examples of aryloxyalkyl, heteroaryloxyalkyl, arylthioalkyl, or heteroarylthioalkyl moieties include, but are not limited to, chemical groups such as $C_6H_5OCH_2$—, $C_6H_5OCH(CH_3)$—, 4-pyridyl-O—$CH_2CH_2$—, $C_6H_5SCH_2$—, $C_6H_5SCH(CH_3)$—, 4-pyridyl-S—$CH_2CH_2$—, and homologs, isomers, and the like. It is preferred that straight chain aryloxyalkyl, heteroaryloxyalkyl, arylthioalkyl, or heteroarylthioalkyl moieties have 1-6 carbon atoms, and branched aryloxyalkyl, heteroaryloxyalkyl, arylthioalkyl, or heteroarylthioalkyl moieties have 3-8 carbon atoms.

The term "alkylamino", employed alone or in combination with other terms, or unless otherwise stated, is a moiety with one alkyl group, wherein the alkyl group is an unsubstituted ($C_1$-$C_8$) straight chain hereunto before defined alkyl group or an unsubstituted ($C_3$-$C_8$) hereunto before defined cycloalkyl group. Examples of alkylamino moieties include, but are not limited to, chemical groups such as —$NH(CH_3)$, —$NH(CH_2CH_3)$, —NH-cyclopentyl, and homologs, and the like.

The term "dialkylamino", employed alone or in combination with other terms, or unless otherwise stated, is a moiety with two independent alkyl (including cycloalkyl) groups, wherein the alkyl groups are unsubstituted ($C_1$-$C_6$) straight chain hereunto before defined alkyl groups or unsubstituted ($C_3$-$C_8$) hereunto before defined cycloalkyl groups. Two groups may be linked to form an unsubstituted ($C_2$-$C_6$)-alkylene-group. Examples of dialkylamino moieties include, but are not limited to, chemical groups such as —N(CH$_3$)$_2$, —N(CH$_2$CH$_3$)$_2$, —NCH$_3$(CH$_2$CH$_3$),

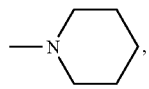

and homologs, and the like.

The term "alkylaminoalkyl" employed alone or in combination with other terms, or unless otherwise stated, is an alkylamino moiety, as herein before defined, which is further covalently bonded to a straight chain alkyl group of 1-6 carbon atoms. Examples of alkylaminoalkyl moieties include, but are not limited to, chemical groups such as —CH$_2$NH (CH$_3$), —CH$_2$CH$_2$NH(CH$_2$CH$_3$), —CH$_2$CH$_2$CH$_2$NH (CH$_2$CH$_3$), and homologs, and the like.

The term "dialkylaminoalkyl" employed alone or in combination with other terms, or unless otherwise stated, is a dialkylamino moiety, as herein before defined, which is further covalently bonded to a straight chain alkyl group of 1-6 carbon atoms. Examples of dialkylaminoalkyl moieties include, but are not limited to, chemical groups such as —CH$_2$N(CH$_3$)$_2$, —CH$_2$CH$_2$N(CH$_2$CH$_3$)$_2$, —CH$_2$CH$_2$CH$_2$NCH$_3$(CH$_2$CH$_3$), and homologs, and the like.

The terms "alkylaminocarbonyl" or "dialkylaminocarbonyl", employed alone, or unless otherwise stated, are alkylamino or dialkylamino moieties, as herein before defined, which are further bonded to a carbonyl group. Examples of alkylaminocarbonyl or dialkylaminocarbonyl moieties include, but are not limited to, chemical groups such as —C(O)NH(CH$_3$), —C(O)N(CH$_2$CH$_3$)$_2$, —C(O)NCH$_3$ (CH$_2$CH$_3$), and homologs, and the like.

Each of the above terms (e.g., alkyl, aryl, heteroaryl) includes unsubstituted, monosubstituted, and polysubstituted forms of the indicated radical or moiety. Substituents for each type of moiety are provided below.

Substituents for alkyl, alkenyl, alkynyl, cycloalkyl, cycloalkenyl, alkylene, cycloalkylene, the alkyl portion of arylalkyl and heteroarylalkyl, saturated or partially saturated heterocyclic rings, and acyl or carbonyl moieties are, employed alone or in combination with other terms, selected from the group consisting of —R', OR', =O, =NR', =N—OR', —NR'R", —SR', halo, trifluoromethyl, trifluoromethoxy, —OC(O)R', —CO$_2$R', —C(O)NR'R", —OC(O) NR'R", —NR"C(O)R', —NR"CO$_2$R', —NR'C(O)NR'R", —NH—C(NH$_2$)=NH, —NR'C(NH$_2$)=NH, —NH—C (NH$_2$)=NR', —S(O)R', —S(O)$_2$R', —S(O)$_2$NR'R", cyano, and nitro; wherein, R' or R" are each, independently, hydrogen, unsubstituted (C$_1$-C$_6$)alkyl, unsubstituted (C$_3$-C$_7$)cycloalkyl, aryl, aryl-(C$_1$-C$_3$)alkyl, aryloxy-(C$_1$-C$_3$)alkyl, arylthio-(C$_1$-C$_3$)alkyl, heteroaryl, heteroaryl-(C$_1$-C$_3$)alkyl, heteroaryloxy-(C$_1$-C$_3$)alkyl, or heteroarylthio-(C$_1$-C$_3$)alkyl groups; or if optionally taken together may be linked as an -alkylene-group eg 2-6 carbon atoms, to form a ring.

The aryl or heteroaryl moieties, employed alone or in combination with other terms, may be optionally mono-, di- or tri-substituted with substituents selected from the group consisting of —R', —OR', —SR', —C(O)R', —CO$_2$R', -alkoxyalkyl, alkoxyalkyloxy, cyano, halogen, nitro, trifluoromethyl, trifluoromethoxy, —NR'R", alkylaminoalkyl, dialkylaminoalkyl, hydroxyalkyl, —S(O)R', —S(O)$_2$R', —SO$_3$R', —S(O)$_2$NR'R", —CO$_2$R', —C(O)NR'R", —OC(O)NR'R", —NR"C(O)R', —NR"CO$_2$R', —NR'C(O)NR'R", —NH—C (NH$_2$)=NH, —NR'C(NH$_2$)=NH, —NH—C(NH$_2$)=NR', —S(O)R', and —S(O)$_2$R'; wherein, R' or R" are each, independently, hydrogen, (C$_1$-C$_6$)alkyl, (C$_3$-C$_7$)cycloalkyl, aryl, aryl-(C$_1$-C$_3$)alkyl, aryloxy-(C$_1$-C$_3$)alkyl, arylthio-(C$_1$-C$_3$) alkyl, heteroaryl, heteroaryl-(C$_1$-C$_3$)alkyl, heteroaryloxy-(C$_1$-C$_3$)alkyl, or heteroarylthio-(C$_1$-C$_3$)alkyl groups; or if optionally taken together may be linked as an -alkylene-group eg 2-6 carbon atoms, to form a ring.

A pro-drug is defined as a compound which is convertible by in vivo enzymatic or non-enzymatic metabolism (e.g. hydrolysis) to a compound of the invention wherein R$_7$ is a hydrogen atom.

The compounds of the present invention may contain an asymmetric atom, and some of the compounds may contain one or more asymmetric atoms or centers, which may thus give rise to optical isomers (enantiomers) and diastereomers. While the formulas herein are shown without respect to the stereochemistry, the compounds of the present invention includes such optical isomers (enantiomers) and diastereomers (geometric isomers); as well as the racemic and resolved, enantiomerically pure R and S stereoisomers; as well as other mixtures of the R and S stereoisomers and pharmaceutically acceptable salts thereof. Optical isomers may be obtained in pure form by standard procedures known to those skilled in the art, and include, but are not limited to, diasteromeric salt formation, kinetic resolution, and asymmetric synthesis. It is also understood that this invention encompasses all possible regioisomers, and mixtures thereof, which may be obtained in pure form by standard separation procedures known to those skilled in the art, and include, but are not limited to, column chromatography, thin-layer chromatography, and high-performance liquid chromatography.

The compounds of the present invention may contain isotopes of atoms for diagnostic, therapeutic, or metabolic purposes. Such isotopes may or may not be radioactive.

The compounds of this invention include racemates, enantiomers, geometric isomers, or pro-drugs of the compounds shown herein.

Pharmaceutically acceptable salts of the compounds of compounds of the instant invention with an acidic moiety can be formed from organic and inorganic bases. Suitable salts with bases are, for example, metal salts, such as alkali metal or alkaline earth metal salts, for example sodium, potassium, or magnesium salts; or salts with ammonia or an organic amine, such as morpholine, thiomorpholine, piperidine, pyrrolidine, a mono-, di- or tri-lower alkylamine, where 'lower' includes 1-6 carbon atoms, for example ethyl-tert-butyl-, diethyl-, diisopropyl-, triethyl-, tributyl- or dimethylpropylamine, or a mono-, di-, or trihydroxy lower alkylamine, for example mono-, di- or triethanolamine. Internal salts may furthermore be formed. Similarly, when a compound of the present invention contains a basic moiety, salts can be formed from organic and inorganic acids. For example salts can be formed from acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known pharmaceutically acceptable acids.

As used in accordance with this invention, the term "providing," with respect to providing a compound or substance covered by this invention, means either directly administering such a compound or substance, or administering a pro-drug, derivative, or analog which will form the effective amount of the compound or substance within the body. This invention also covers providing the compounds of this invention to treat the disease states disclosed herein that the compounds are useful for treating.

Solvates (e.g., hydrates) of the compounds of the present invention are also within the scope of the present invention. Methods of solvation are generally known in the art. Accordingly, the compounds of the instant invention can be in the free or hydrate form, and can be obtained by methods exemplified by the following schemes below.

Also according to the present invention there is provided a method of treating medical conditions which comprises administering to a human or other mammal an anti-inflammatory effective amount of a compound of the present invention. These conditions include atherosclerosis, myocardial infarction, congestive heart failure, arthritis and inflammatory bowel disease in humans or other mammals.

It is understood that the effective dosage of the active compounds of this invention may vary depending upon the particular compound utilized, the mode of administration, the condition, and severity thereof, of the condition being treated, as well as the various physical factors related to the individual being treated. For treating conditions such as atherosclerosis, myocardial infarction, congestive heart failure, arthritis and/or inflammatory bowel disease, generally satisfactory results may be obtained when the compounds of this invention are administered to the individual in need at a daily dosage of from about 0.1 mg to about 1 mg per kilogram of body weight, preferably administered in divided doses two to six times per day, or in a sustained release form. For most large mammals, the total daily dosage is from about 3.5 mg to about 140 mg. In the case of a 70 kg human adult, the total daily dose will generally be from about 7 mg to about 70 mg and may be adjusted to provide the optimal therapeutic result. This regimen may be adjusted to provide the optimal therapeutic response.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elexir may contain, in addition to the active ingredients, sucrose as a sweetening agent, methyl and propyl parabens as preservatives, a dye and a flavoring such as cherry or orange flavor.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, there preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Also according to the present invention there are provided processes for producing the compounds of the present invention.

PROCESS OF THE INVENTION

Compounds of the invention can be readily prepared according to the following reaction schemes or modifications thereof using readily available starting materials, reagents and conventional synthetic procedures. It is also possible to make use of variants of these process steps, which in themselves are known to and well within the preparatory skill of the medicinal chemist.

Some synthetic approaches to compounds of the present invention are described in schemes 1-6. Starting with the readily available 3-thiophene-carboxylic acid, diphenylphosphoryl azide and base in dry tert-butanol (Scheme 1), heating to reflux can yield the tert-butylcarbonyl protected 3-aminothiophene 1 (*J. Heterocycl. Chem.* 1968, 28, 417). Monobromination of the 2-position of the thiophene with N-bromosuccinimide in refluxing carbon tetrachloride can yield the thiophene 2 (*J. Pharm. Sci.* 1968, 5, 2003). Suziki coupling of the thiophene 2 with the boronic acid 3a,b (R=H, CH$_3$) under basic conditions and then refluxing acid gives thienoisoquinolines 4a,b (4a ref. *J. Heterocycl. Chem.* 1989, 26, 865). Reduction with a hydride yields the amine 6, which is sulfonylated with a sulfonyl chloride and base in a halogenated solvent to yield the sulfonamide 7. Demethylation of the methyl ether yields compound 8.

Scheme 1

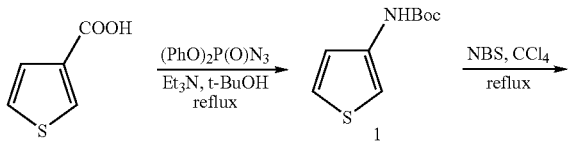

-continued
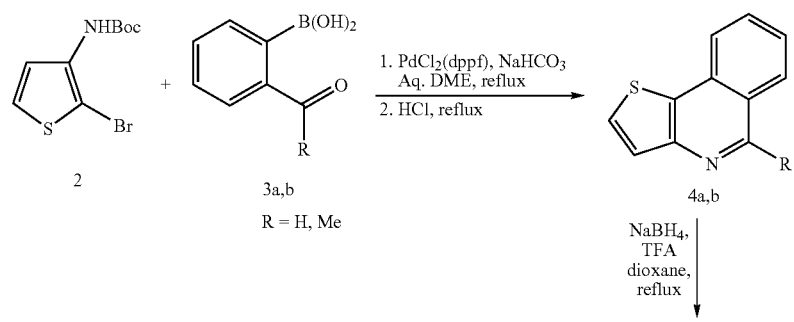
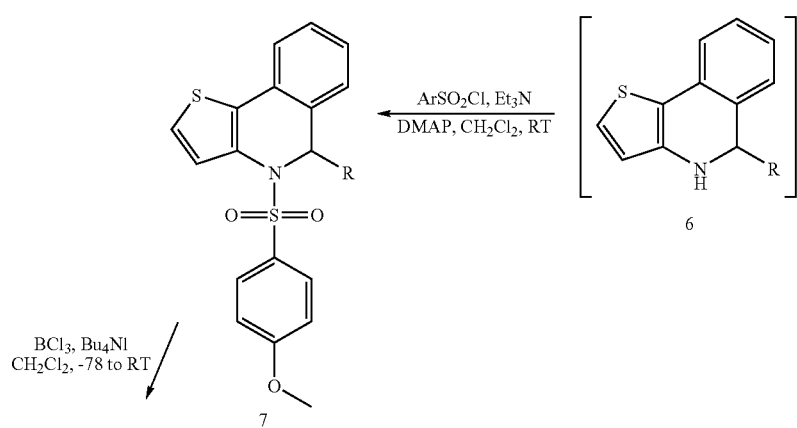
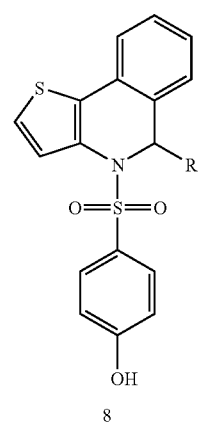

Alternatively, thienoisoquinoline 4a can be oxidized to the N-oxide 5 with metachloro-peroxybenzoic acid in a halogenated solvent at room temperature. Reaction of the N-oxide 5 with a Grignard reagent, such as ethyl magnesium bromide in ether at room temperature can yield the ethyl substituted (R=ethyl) thienoisoquinoline 4c. Hydride reduction to the intermediate amine 6, followed by reaction with an aryl sulfonyl chloride with base can be used to produce compound 7. Demethylation of the methyl ether can produce certain compounds of the present invention.

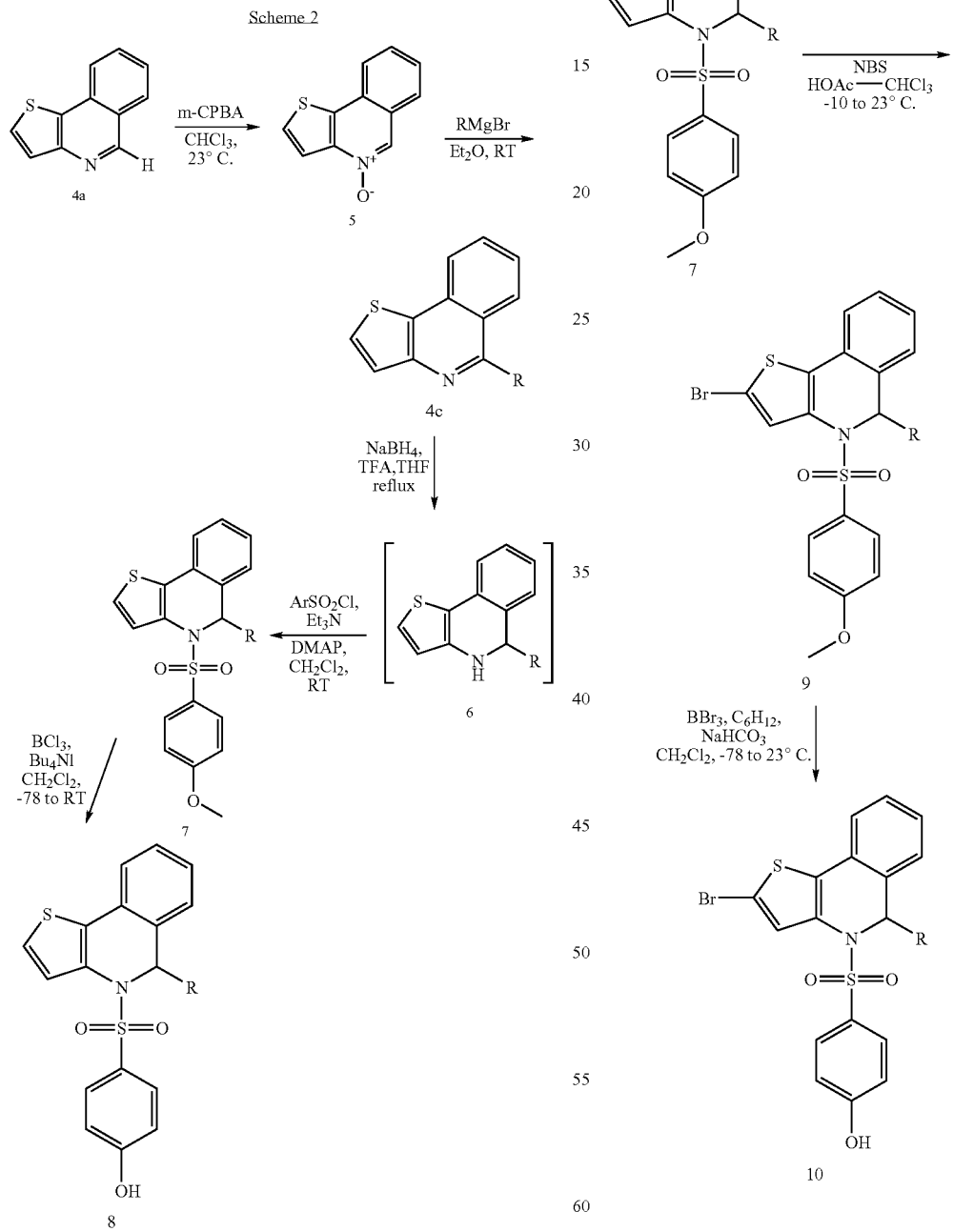

Halogenated thieno-isoquinolines can be synthesized from 4-alkoxyphenyl sulfonamide 7 by reaction with N-bromosuccinimide in acetic acid-chloroform at −10° C. to room temperature to yield the mono-bromothienoisoquinoline 9 (Scheme 3). Dealkylation of the alkyl phenol with boron tribromide, cyclohexene, sodium bicarbonate in a halogenated solvent at −78° C. to room temperature yields bromo substituted thieno-isoquinoline sulfonamide 10.

Halogenated thienoisoquinolines can alternatively be synthesized from 4-hydroxyphenyl sulfonamide 8 by reaction with N-bromosuccinimide in acetic acid-chloroform at room temperature to yield the target compound 10 (Scheme 4), along with a dibromo compound and a tribromo compound.

Scheme 4

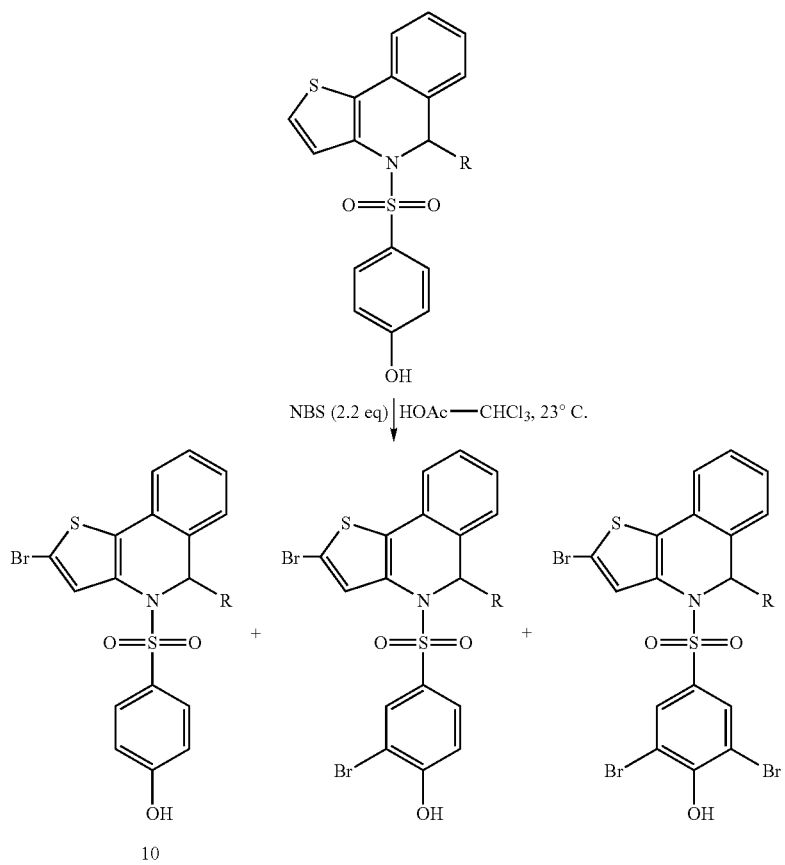

The bromo-substituted thienoisoquinoline 9 can be reacted with an arylboronic acid or a heteroarylboronic acid in a Suzuki coupling with a palladium catalyst and base in an aqueous or non-aqueous solvent to yield an aryl or heteroaryl substituted thienoisoquinoline product 11 (Scheme 5). Demethylation of the methyl ether with boron tribromide, cyclohexene and base in a halogenated solvent yields the thienoisoquinoline sulfonamide 12.

-continued

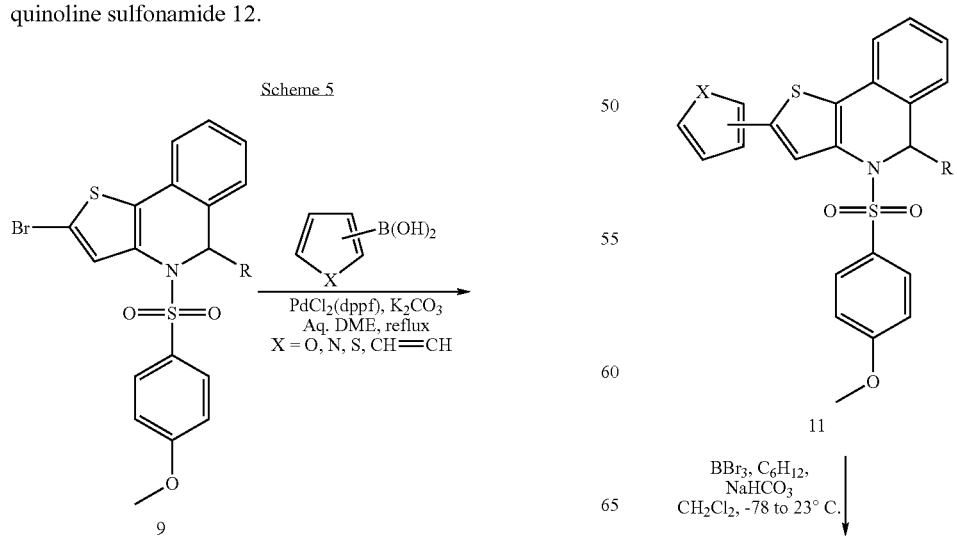

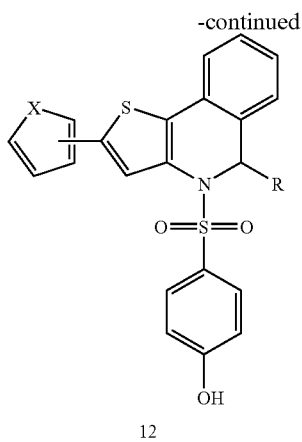

12

The halogen substituted thieno-isoquinoline sulfonamide 9 reacts with n-butyllithium then dimethylformamide to yield the carboxaldehyde 13 (Scheme 6). Wittig reaction of the aldehyde yields the corresponding alkene 14. Demethylation of the methyl ether with boron tribromide, base, cyclohexene in a halogenated solvent yields the alkene substituted thienoisoquinoline sulfonamide 15. The Wittig product 14 can also be treated with hydrogen and a palladium catalyst to yield, after work-up, the saturated compound 16. The demethylation of the methyl ether as mentioned previously yields the alkyl substituted thienoisoquinoline sulfonamide 17.

Scheme 6

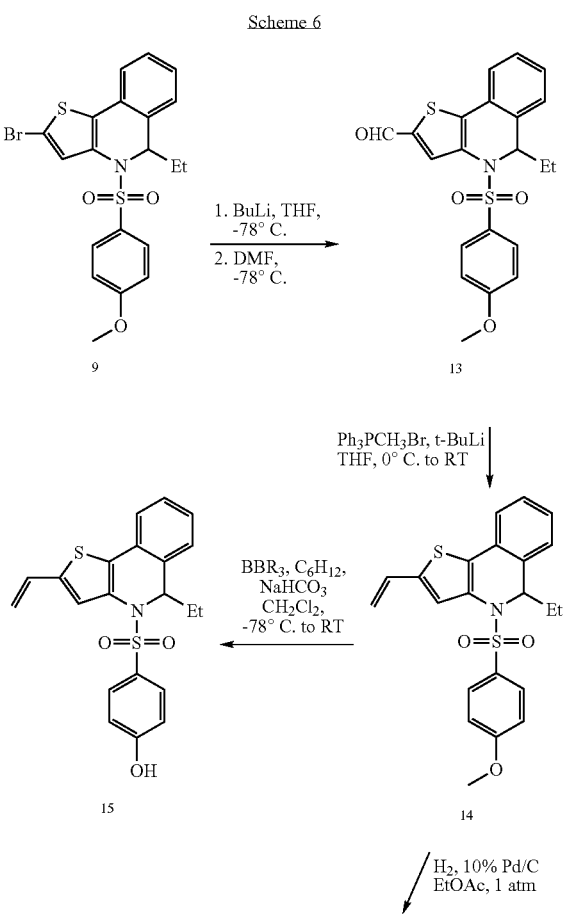

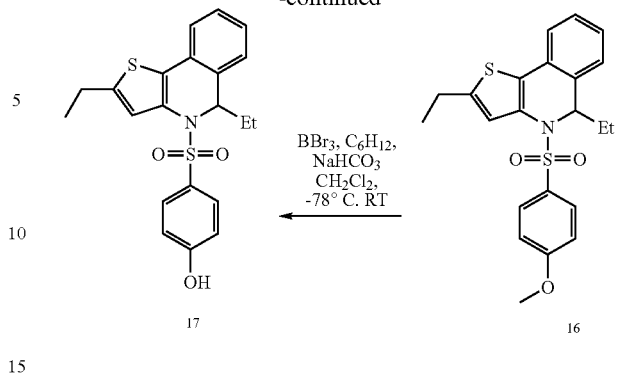

The following non-limiting examples further illustrate this invention.

EXPERIMENTAL

Commercially available reagents and solvents were used directly as received except for N-bromosuccinimide which was recrystallized from water. All procedures employing air- and/or moisture-sensitive reagents were conducted under an inert atmosphere in flame-dried glassware where appropriate. $^1$H NMR spectra were recorded in DMSO-$d_6$ on a Varian Inova spectrometer at 500 MHz, unless otherwise indicated.

EXAMPLE 1

Thieno[3,2-c]isoquinoline (Compound 4a)

Step 1: tert-Butyl thien-3-ylcarbamate (Compound 1)

3-Thiophenecarboxylic acid (31 g, 0.24 mol), Diphenylphosphoryl azide (57 mL, 0.26 mol) and triethylamine (36 mL, 0.26 mol) were combined in dry tert-butanol (450 mL) and the resulting solution was heated to reflux. After 22 h the cooled solution was concentrated in vacuo to remove solvent. The residue was taken up in diethyl ether (1.5 L) and washed with 5% aqueous citric acid, water and brine (1.5 L each), dried (Na$_2$SO$_4$), and concentrated in vacuo to give the crude product as a tacky tan solid (51 g). Recrystallization from hot ethyl acetate-hexane gave the title compound (33 g, 69%, m.p. 139-41° C.) as shiny off-white needles.

$^1$H NMR δ 1.45 (s, 9 H, (CH$_3$)$_3$), 6.97 (m, 1 H, ArH), 7.16 (broad s, 1 H, ArH), 7.37 (m, 1 H, ArH), 9.60 (broad s, 1 H, NH). MS (ESI) m/z 198 [M−H]$^-$ Analysis calc. for C$_{18}$H$_{13}$FO$_3$S: C, 54.25; H, 6.58; N, 7.03. Found: C, 54.26; H, 6.48; N, 6.99.

Step 2: tert-Butyl 2-bromothien-3-ylcarbamate (Compound 2)

Tert-butyl thien-3-ylcarbamate (37 g, 0.19 mol) and N-bromosuccinimide (33 g, 0.19 mol) were combined in carbon tetrachloride (900 mL) and heated at reflux for 3 h. At this time, the mixture was cooled to 23° C. and filtered. The filtrate was washed with water (5×900 mL) to remove succinimide, dried (Na$_2$SO$_4$), and concentrated in vacuo to give the title compound (50 g, 96%, m.p. 68-70° C.) as a tan solid which was pure enough for further use.

$^1$H NMR δ 1.43 (s, 9 H, (CH$_3$)$_3$), 7.09 (d, J=6 Hz, 1 H, ArH), 7.51 (d, J=6 Hz, 1 H, ArH), 8.74 (broad s, 1 H, NH). MS (ESI) m/z 276 [M−H]$^-$ Analysis calc. for C$_9$H$_{12}$BrNO$_2$S: C, 38.86: H. 4.35: N, 5.04. Found: C, 38.66: H. 4.10: N, 4.99.

Step 3: Thieno[3,2-c]isoquinoline (Compound 4a)

Tert-butyl 2-bromothien-3-ylcarbamate (35 g, 0.13 mol), 2-Formylphenylboronic acid (Cmpd IIIa, 25 g, 0.17 mol), [1,1'-Bis(diphenylphosphino)ferrocene]dichloropalladium [II] (5.3 g, 6.5 mmol), and sodium bicarbonate (33 g, 0.39 mol) were combined in 40% aqueous dimethoxyethane (675 mL) and the mixture was heated to reflux. After 1 h the mixture was cooled to 23° C., treated slowly with 2 N aqueous hydrochloric acid (405 mL) and heated back to reflux for an additional 2 h. At this time the mixture was cooled to 23° C., treated slowly with 2.5 N aqueous sodium hydroxide (270 mL) and stirred for ca. 15 min. The mixture was filtered through Celite and washed with ethyl acetate (2.2 L). The organic layer was separated from the filtrate and washed with water and brine (2.2 L each), dried ($K_2CO_3$), and concentrated in vacuo to give the crude product (28 g) as a dark oil. The oil was taken up in methylene chloride (75 mL) and pre-adsorbed on silica gel (75 g). Flash chromatography on silica gel (725 g) eluting 5-, then 10-, and then 20% ethyl acetate-hexane gave the title compound (19 g, 83%, m.p. 58-61° C.) as a yellow-brown solid which was pure enough for further use.

$^1$H NMR δ 7.71-7.74 (overlapping m, 2H, ArH), 7.89 (m, 1H, ArH), 8.06 (d, J=5.3 Hz, 1H, ArH), 8.17 (m, 1H, ArH), 8.27 (d, J=8 Hz, 1H, ArH), 9.29 (s, 1H, ArH). MS (ESI) m/z 186 [M+H]$^+$ Analysis calc. for $C_{11}H_7NS$: C, 71.32; H, 3.81; N, 7.56. Found: C, 71.33; H, 3.79; N, 7.23.

EXAMPLE 2

5-Methylthieno[3,2-c]isoquinoline (Compound 4b)

Starting from 2-Acetylphenylboronic acid (15 g, 91 mmol) in place of 2-formylphenylboronic acid in Step 3, the title compound (12 g, 86%, m.p. 74-76° C.) was synthesized in essentially the same manner as described in Steps 1-3 for Thieno[3,2-c]isoquinoline.

$^1$H NMR δ 2.95 (s, 3H, CH$_3$), 7.62 (m, 1H, ArH), 7.71 (m, 1H, ArH), 7.86 (m, 1H, ArH), 7.98 (m, 1H, ArH), 8.13 (d, J=8 Hz, 1H, ArH), 8.32 (d, J=8 Hz, 1H, ArH). MS (ESI) m/z 200 [M+H]$^+$ Analysis calc. for $C_{12}H_9NS$: C, 72.33: H, 4.55; N. 7.03. Found: C. 72.13; H, 4.70: N, 7.01.

EXAMPLE 3

5-Ethylthieno[3,2-c]isoquinoline (Compound 4c)

Step 1: Thieno[3,2-c]isoquinoline-4-oxide (Compound 5)

Thieno[3,2-c]isoquinoline (13 g, 71 mmol) and 3-Chloroperoxybenzoic acid (57-86%, 21 g, 71 mmol) were combined in chloroform (300 mL) at 23° C. After 3 days the mixture was diluted with chloroform (750 mL), washed with 10% aqueous sodium hydroxide (2×500 mL) and brine (500 mL), dried (MgSO$_4$), and concentrated in vacuo to give the crude product (13 g) as a yellow-brown solid. Recrystallization from hot ethanol (ca. 75 mL) provided the title compound (9.4 g, 66%, m.p. 190-95° C.) as dense brown needles.

$^1$H NMR δ 7.67 (m, 1H, ArH), 7.71 (m, 1H, ArH), 7.84 (d, J=5.5 Hz, 1H, ArH), 8.01 (d, J=8 Hz, 1H, ArH), 8.10 (d, J=5.5 Hz, 1H, ArH), 8.12 (d, J=1H, ArH), 9.01 (s, 1H, ArH). MS (ESI) m/z 202 [M+H]$^+$ Analysis calc. for $C_{11}H_7NOS$: C, 65.65; H, 3.51; N, 6.96. Found: C, 65.46; H, 3.46; N, 6.89.

Step 2: 5-Ethylthieno[3,2-c]isoquinoline (Compound 4c)

A suspension of Thieno[3,2-c]isoquinoline 4-oxide (20 g, 99 mmol) in dry tetrahydrofuran (ca. 400 mL) was treated dropwise at −78° C. with an ethereal solution of ethylmagnesium bromide (3.0 M, 40 mL, 120 mmol) during 10 min. After 6 h the reaction mixture was quenched with 2 N aqueous hydrochloride acid (75 mL) and stirred for ca. 10 min. At this time the solution was treated with 2.5 N aqueous sodium hydroxide (65 mL). The resulting gelatinous residue was diluted with water (400 mL), filtered through Celite, and the filtrate was extracted with ethyl acetate (3×500 mL). The combined extracts were washed with water and brine (1.5 L each), dried ($K_3CO_3$) and concentrated in vacuo to give the crude product (19 g) as an orange oil which was taken up in methylene chloride (ca. 60 mL) and pre-adsorbed on silica gel (60 g). Flash chromatography on silica gel (740 g) eluting 2.5-, then 5-, and then 10% ethyl acetate-hexane provided the title compound (17 g, 81%, m.p. 39-41° C.) as a clear, pale yellow oil which crystallized on standing.

$^1$H NMR δ 1.38 (m, 3H, CH$_2$CH$_3$), 3.36 (m, 2H, CH$_2$CH$_3$), 7.65 (d, J=5.4 Hz. 1H, ArH), 7.70 (m, 1H, ArH), 7.86 (m, 1H, ArH), 7.99 (d, J=5.4 Hz, 1H, ArH), 8.14 (d, J=8 Hz, 1H, ArH), 8.37 (d, J=8 Hz, 1H, ArH). MS (EI) m/z 213 [M]$^+$ Analysis calc. for $C_{13}H_{11}NS$: C, 73.20; H, 5.20; N, 6.57. Found: C, 73.18; H, 5.14; N, 6.48.

EXAMPLE 4

4-[(5-Methylthieno[3,2-c]isoquinolin-4(5H)-yl)sulfonyl]phenol (Compound 8a)

Step 1: 5-Methyl-4,5-dihydrothieno[3,2-c]isoquinoline (Compound 6a)

5-Methylthieno[3,2-c]isoquinoline (12 g, 60 mmol) and sodium borohydride (9.0 g, 240 mmol) were combined in dry 1,4-dioxane (200 mL) at 23° C. Trifluoroacetic acid (9.2 mL, 120 mmol) was slowly added via syringe with gentle bubbling. After the addition was complete, the mixture was heated to reflux for 24 h. At this time the mixture was cooled to 23° C., quenched with de-gassed saturated aqueous sodium bicarbonate (450 mL) and extracted under nitrogen with de-gassed methylene chloride (3×ca. 150 mL). The combined extracts were washed under nitrogen with de-gassed brine (ca. 450 mL), dried (Na$_2$SO$_4$) under nitrogen and concentrated in vacuo to give the crude title compound (16 g) as an air-sensitive orange oil.

Step 2: 4-[(4-Methoxyphenyl)sulfonyl]-5-methyl-4,5-dihydrothieno[3,2-c]isoquinoline (Compound 7a)

A solution of 4-Methoxybenzenesulfonyl chloride (16 g, 77 mmol), triethylamine (25 mL, 180 mmol), and 4-dimethylaminopyridine (0.20 g, 1.6 mmol) in methylene chloride (100 mL) was de-gassed with nitrogen and treated with a de-gassed methylene chloride (100 mL) solution of 5-Methyl4,5-dihydrothieno[3,2-c]isoquinoline (16 g obtained above) at 23° C. After 21 h the reaction mixture was quenched with 1 N aqueous sodium hydroxide (200 mL). The organic layer was separated and the aqueous phase was extracted with methylene chloride (2×200 mL). The combined extracts were washed with 1 N aqueous sodium hydroxide, 1 N aqueous hydrochloric acid, and brine (200 mL each), dried (K$_2$CO$_3$), and concentrated in vacuo to give the crude product (21 g) as a dark oil. The oil was taken up in methylene chloride (ca. 80 mL) and pre-adsorbed on silica gel (80 g). Flash chromatography on silica gel (400 g) eluting 25-, then 50-, and then 75% methylene chloride-hexane gave the product (16 g) as a yellow solid. Further elution with methylene chloride, then 10-, and then 20% ethyl acetate-methylene chloride gave recovered 5-methylthieno[3,2-c]isoquinoline (1.7 g, 14%) from the previous step. Recrystallization of the product from hot ethyl acetate-hexane provided the title compound (15 g, 79% overall based on recovered starting material from Step 1, m.p. 135-36° C.) as shiny yellow-orange prisms.

$^1$H NMR (400 MHz) δ 1.19 (d, J=7 Hz, 3H, CHCH$_3$), 3.63 (s, 3H, OCH$_3$), 5.43 (m, 1H, CHCH$_3$), 6.64 (d, J=9 Hz, 2H, ArH), 7.01-7.13 (overlapping m, 5H, ArH), 7.22-7.26 (overlapping m, 2H, ArH), 7.57 (d, J=5.3 Hz, 1H, ArH). MS (ESI) m/z 372 [M+H]$^+$ Analysis calc. for C$_{19}$H$_{17}$NO$_3$S$_2$: C, 61.43: H, 4.61; N, 3.77. Found: C, 61.31: H, 4.56; N, 3.69.

Step 3: 4-[(5-Methylthieno[3,2-c]isoquinolin-4(5H)-yl)sulfonyl]phenol (Compound 8a)

A solution of 4-[(4-methoxyphenyl)sulfonyl]-5-methyl-4,5-dihydrothieno[3,2-c]isoquinoline (0.45 g, 1.2 mmol) and tetrabutylammonium iodide (1.33 g, 3.6 mmol) in dry methylene chloride (9 mL) was treated dropwise with a solution of boron trichloride in methylene chloride (1.0 M, 3.6 mL, 3.6 mmol) at −78° C. during ca. 5 min. After a further 5 min., the solution was warmed to 23° C. After 16 h the reaction solution was concentrated in vacuo and the residue was taken up in ethyl acetate (25 mL). The organic phase was washed with saturated aqueous sodium bicarbonate (25 mL) and water (10×25 mL), dried (MgSO$_4$), and concentrated in vacuo to give a dark, oily solid (0.68 g) which was suspended in 20% ethyl acetate-hexane and slurried onto a column of silica gel (10 g). Flash chromatography eluting 20-, and then 30% ethyl acetate-hexane gave the product (0.35 g) as a yellow solid. Recrystallization from hot ethyl acetate-hexane gave the title compound (0.28 g, 65%, m.p. 163-65° C.) as shiny white needles.

$^1$H NMR (400 MHz) δ 1.18 (d, J=7 Hz, 3H, CHCH$_3$), 5.41 (m, 1H, CHCH$_3$), 6.42 (d, J=9 Hz, 2H, ArH), 7.00-7.14 (overlapping m, 5H, ArH), 7.22-7.24 (overlapping m, 2H, ArH), 7.56 (d, J=5 Hz, 1H, ArH), 10.3 (broad s, 1H, ArOH). MS (ESI) m/z 356 [M−H]$^-$ Analysis calc. for C$_{18}$H$_{15}$NO$_3$S$_2$: C, 60.48; H, 4.23; N, 3.92. Found: C, 60.45; H, 4.11; N, 3.75.

EXAMPLE 5

4-[(5-Ethylthieno[3,2-c]isoquinolin-4(5H)-yl)sulfonyl]phenol (Compound 8b)

Starting from 5-ethylthieno[3,2-c]isoquinoline (12.8 g, 60 mmol) in place of 5-methylthieno[3,2-c]isoquinoline in Step 1, the title compound (23 mg white solid, 24%, m.p. 169-71° C.) was synthesized in essentially the same manner as described in Example 1, Steps 1-3, for 4-[(5-Methylthieno[3,2-c]isoquinolin-4(H)-yl)sulfonyl]phenol.

$^1$H NMR δ 0.89 (m, 3H, CH$_2$CH$_3$), 1.41 (m, 2H, CH$_2$CH$_3$), 5.10 (m, 1H, CHCH$_2$), 6.42 (d, J=9 Hz, 2H, ArH), 7.00-7.04 (overlapping m, 3H, ArH), 7.08-7.14 (overlapping m, 2H, ArH), 7.21 (d, J=8 Hz, 1H, ArH), 7.24 (d, J=5 Hz, 1H, ArH), 7.55 (d, J=5 Hz, 1H, ArH), 10.2 (s, 1H, ArOH). HRMS calc. for C$_{19}$H$_{16}$NO$_3$S$_2$ [M−H]$^-$: 370.05770. Found (ESI): 370.05778.

Method A

EXAMPLE 6

4-[(2-Bromo-5-methylthieno[3,2-c]isoquinolin-4 (5H)-yl)sulfonyl]phenol (Compound 10a)

4-[(5-Methylthieno[3,2-c]isoquinolin4(H)-yl)sulfonyl] phenol (0.24 g, 0.67 mmol) and N-bromosuccinimide (0.12 g, 0.67 mmol) were combined in 1:1 acetic acid-chloroform (5 mL) at 23° C. After 24 h the resulting solution was diluted with chloroform (45 mL) and washed with water, 25% aqueous potassium hydroxide, 1 N aqueous hydrogen chloride and brine (50 mL each), dried (MgSO$_4$) and concentrated in vacuo to give the crude product (0.28 g). Reverse phase HPLC (25×5 cm Primesphere 10 C$_{18}$ column, 40% aqueous acetonitrile with 0.1% formic acid @ 100 mL/min) gave the title compound (0.12 g, 41%, m.p. 209-11° C.) as a white solid.

$^1$H NMR δ (d, J=7 Hz, 3H, CHCH$_3$), 5.37 (m, 1H, CHCH$_3$), 6.47 (d, J=9 Hz, 2H, ArH), 7.00 (d, J=7.5 Hz, 1H, ArH), 7.07-7.11 (overlapping m, 3H, ArH), 7.14 (m, 1H, ArH), 7.22 (d, J=7.5 Hz, 1H, ArH), 7.34 (s, 1H, ArH), 10.3 (s, 1H, ArOH). HRMS calc. for C$_{18}$H$_{13}$BrNO$_3$S$_2$ [M−H]$^-$ 433.95257. Found (ESI) 433.95249.

Method B

4-[(4-methoxyphenyl)sulfonyl]-5-methyl-4,5-dihydrothieno[3,2-c]isoquinoline was separated via chiral HPLC utilizing a Chiralpak AS column and 9:1 methanol:water as an eluent at 0.6 mL/min to yield the two enantiomerically enriched compounds.

EXAMPLE 7

Step 1: (5R)-2-bromo-4-[(4-methoxyphenyl)sulfonyl]-5-methyl-4,5-dihydrothieno[3,2-c]isoquinoline (Compound 9a)

A solution of (5R)4-[(4-methoxyphenyl)sulfonyl]-5-methyl-4,5-dihydrothieno[3,2-c]isoquinoline (12.7 g, 34 mmol) in 1:1 acetic acid-chloroform (300 mL) was treated with N-bromosuccinimide (6.1 g, 34 mmol) at −10° C. After ca. 5 min., the cooling bath was removed and the mixture was warmed to 23° C. After 18 h the resulting solution was poured into water (1.2 L) and extracted with methylene chloride (4×400 mL). The organic solution was washed with 25% aqueous potassium hydroxide and brine (1 L each), dried (K$_2$CO$_3$), and concentrated in vacuo to give the crude product (15.5 g) as a green solid which was loaded onto a column of silica gel (100 g) in warm 25% methylene chloride-hexane. Flash chromatography eluting 25-, then 50-, and then 75% methylene chloride-hexane gave the title compound (15.1 g, 98%, m.p. 136-38° C.) as a white solid. [α]$_D$=+219.4. $^1$H NMR (400 MHz) δ 1.21 (d, J=7 Hz, CHCH$_3$), 3.64 (s, 3H, OCH$_3$), 5.40 (m, 1H, CHCH$_3$), 6.69 (d, J=9 Hz, 2H, ArH), 6.98 (d, J=7.5 Hz, 1H, ArH), 7.08 (m, 1H, ArH), 7.14 (m, 1H, ArH), 7.16-7.23 (overlapping m, 3H, ArH), 7.36 (s, 1H, ArH). MS (ESI) m/z 450 [M+H]$^+$ Analysis calc. for C$_{19}$H$_{16}$BrNO$_3$S$_2$: C, 50.67: H, 3.58; N, 3.11. Found: C, 50.68; H, 3.37; N, 3.04

Step 2: 4-{[(5R)-2-bromo-5-methylthieno[3,2-c] isoquinolin-4-(5H)-yl]sulfonyl}phenol (Compound 10a)

A solution of (5R)-2-bromo-4-[(4-methoxyphenyl)sulfonyl]-5-methyl-4,5-dihydrothieno[3,2-c]isoquinoline (2.0 g, 4.4 mmol) in cyclohexene (34 mL) was treated with sodium bicarbonate (11 g, 130 mmol) and the mixture was cooled to −78° C. A solution of boron tribromide in methylene chloride (1.0 M, 22 mL, 22 mmol) was added dropwise during ca. 10 min. At this time the cooling bath was removed and the reaction mixture was warmed to 23° C. After 75 min the mixture was poured into saturated aqueous sodium bicarbonate (200 mL) and extracted with ethyl acetate (100 mL). The extract was washed with water and brine (100 mL each), dried (Na$_2$SO$_4$), and concentrated in vacuo to give a yellow gum (3.3 g) which was taken up in methylene chloride (ca. 5 mL)

and pre-adsorbed on silica gel (5 g). Flash chromatography on silica (145 g) eluting methylene chloride, then 1-, and then 2% ethyl acetate-methylene chloride gave the title compound (0.81 g, 43%, m.p. 209-11° C.) as a pale yellow solid. The analytical sample (EtOAc-hexane) gave pale yellow plates. $[\alpha]_D$=+222.4.

$^1$H NMR δ 1.20 (d, J=7 Hz, 3H, CHCH$_3$), 5.37 (m, 1H, CHCH$_3$), 6.47 (d, J=9 Hz, 2H, ArH), 7.00 (d, J=7.5 Hz, 1H, ArH), 7.07-7.11 (overlapping m, 3H, ArH), 7.14 (m, 1H, ArH), 7.22 (d, J=7.5 Hz, 1H, ArH), 7.34 (s, 1H, ArH), 10.3 (s, 1H, ArOH). MS (ESI) m/z 434 [M−H]$^−$ Analysis calc. for C$_{18}$H$_{14}$BrNO$_3$S$_2$: C, 49.55; H, 3.23; N, 3.21. Found: C, 49.45, H. 3.25: N, 3.10.

EXAMPLE 8

4-{[(5S)-2-bromo-5-methylthieno[3,2-c]isoquinolin-4-(5H)-yl]sulfonyl}phenol

This compound was synthesized in the same manner as in Example 7. $[\alpha]_D$=−245.

EXAMPLE 9

4-[(2-Bromo-5-ethylthieno[3,2-c]isoquinolin-4(5H)-yl)sulfonyl]phenol

Starting from 4-[(4-Methoxyphenyl)sulfonyl]-5-ethyl-4,5-dihydrothieno[3,2-c]isoquinoline in place of 4-[(4-Methoxyphenyl)sulfonyl]-5-methyl-4,5-dihydrothieno[3,2-c]isoquinoline (Step 1), the title compound (0.19 g tan solid, 20%, m.p. 183-85° C.) was synthesized in essentially the same manner as described in Example 6, Method B, Steps 1-2, for 4-[(2-Bromo-5-methylthieno[3,2-c]isoquinolin-4(5H)-yl) sulfonyl]phenol.

$^1$H NMR δ 0.89 (m, 3H, CH$_2$CH$_3$), 1.43 (m, 2H, CH$_2$CH$_3$), 5.07 (m, 1H, CHCH$_2$), 6.46 (d, J=9 Hz, 2H, ArH), 7.00 (d, J=7.5 Hz, 1H, ArH), 7.08-7.11 (overlapping m, 3H, ArH), 7.14 (m, 1H, ArH), 7.21 (d, J=7 Hz, 1H, ArH), 7.34 (s, 1H, ArH), 10.2 (broad s, 1H, ArOH). HRMS calc. for C$_{19}$H$_{17}$BrNO$_3$S$_2$ [M+H]$^+$: 449.98278. Found (ESI): 449.98221.

EXAMPLE 10

4-[(5-Ethyl-2-thien-3-ylthieno[3,2-c]isoquinolin-4(5H)-yl)sulfonyl]phenol (Compound 12a)

Step 1: 5-Ethyl-4-[(4-methoxyphenyl)sulfonyl]-2-thien-3-yl-4,5-dihydrothieno[3,2-c]isoquinoline (Compound 11a)

2-Bromo-5-ethyl-4-[(4-methoxyphenyl)sulfonyl]-4,5-dihydrothieno[3,2-c]isoquinoline (1.02 g, 2.2 mmol), 3-thiopheneboronic acid (0.37 g, 2.9 mol), potassium carbonate (0.91 g, 6.6 mol) and [1.1'-bis(diphenylphosphino)ferrocene]dichloropalladium[II] (90 mg, 0.11 mmol) were combined in 40% aqueous dimethoxyethane (11 mL) and the mixture was heated to 75° C. After 3.5 h the mixture was cooled to 23° C., filtered through Celite and washed with ethyl acetate (125 mL). The filtrate was washed with 1 N aqueous sodium hydroxide and brine (125 mL each), dried (K$_2$CO$_3$), and concentrated in vacuo to give the crude product (0.91 g) as a tan solid which was taken up in methylene chloride (ca. 3 mL) and pre-adsorbed on silica gel (3 g). Flash chromatography on silica gel (27 g) eluting 25-, and then 50% methylene chloride-hexane gave the title compound (0.73 g, 71%, m.p. 182-84° C.) as a white solid which was pure enough for further use.

$^1$H NMR δ 0.93 (m, 3H, CH$_2$CH$_3$), 1.46 (m, 2H, CH$_2$CH$_3$), 3.63 (s, 3H, OCH$_3$), 5.13 (m, 1H, CHCH$_2$), 6.66 (d, J=9 Hz, 2H, ArH), 7.00 (d, J=8 Hz, 1H, ArH), 7.08-7.14 (overlapping m, 2H, ArH), 7.19 (d, J=9 Hz, 2H, ArH), 7.22 (d, J=8 Hz, 1H, ArH), 7.53 (m, 1H, ArH), 7.56 (s, 1H, ArH), 7.69 (m, 1H, ArH), 7.90 (m, 1H, ArH). HRMS calc. for C$_{24}$H$_{22}$NO$_3$S$_3$ [M+H]$^+$: 468.07564. Found (ESI): 468.07667.

Step 2: 4-[(5-Ethyl-2-thien-3-ylthieno[3,2-c]isoquinolin-4(5H)-yl)sulfonyl]phenol (Compound 12a)

A suspension of 5-ethyl-4-[(4-methoxyphenyl)sulfonyl]-2-thien-3-yl-4,5-dihydrothieno[3,2-c]isoquinoline (0.73 g, 1.6 mmol) in cyclohexene (11 mL) was treated with sodium bicarbonate (4.0 g, 48 mmol) and the mixture was cooled to −78° C. A solution of boron tribromide in methylene chloride (1.0 M, 6.4 mL, 6.4 mmol) was added dropwise during ca. 10 min. At this time the cooling bath was removed and the reaction mixture was warmed to 23° C. After 4 h the mixture was poured into saturated aqueous sodium bicarbonate (75 mL) and extracted with ethyl acetate (50 mL). The extract was washed with brine (75 mL), dried (Na$_2$SO$_4$), and concentrated in vacuo to give a dark oil (2.1 g) which was taken up in methylene chloride (ca. 5 mL) and pre-adsorbed on silica gel (5 g). Flash chromatography on silica (50 g) eluting 1.25-, and then 2.5% ethyl acetate-benzene gave the product (0.26 g) as a yellow solid. Recrystallization from hot ethyl acetate-hexane gave the title compound (0.15 g, 21%, m.p. 195-96° C.) as shiny tan needles.

$^1$H NMR δ 0.92 (m, 3H, CH$_2$CH$_3$), 1.46 (m, 2H, CH$_2$CH$_3$), 5.10 (m, 1H, CHCH$_2$), 6.44 (d, J=9 Hz, 2H, ArH), 7.01 (m, 1H, ArH), 7.08 (d, J=9 Hz, 2H, ArH), 7.10-7.14 (overlapping m, 2H, ArH), 7.21 (m, 1H, ArH), 7.52 (m, 1H, ArH), 7.55 (s, 1H, ArH), 7.68 (m, 1H, ArH), 7.89 (m, 1H, ArH), 10.2 (s, 1H, ArOH). MS (ESI) m/z 452 [M−H]$^−$ Analysis calc. for C$_{23}$H$_{19}$NO$_3$S$_3$: C, 60.90: H, 4.22; N, 3.09. Found: C, 60.81; H, 4.20; N, 2.95.

EXAMPLE 11

4-[(5-Ethyl-2-phenylthieno[3,2-c]isoquinolin-4(5H)-yl)sulfonyl]phenol (Compound 12b)

Starting from 2-bromo-5-ethyl-4-[(4-methoxyphenyl)sulfonyl]-4,5-dihydrothieno[3,2-c]isoquinoline (1.02 g, 2.2 mmol) and substituting phenylboronic acid (0.35 g, 2.9 mmol) in place of 3-thiopheneboronic acid in Step 1, the title compound (0.38 g, 50%, m.p. ° C.) was synthesized in essentially the same manner as described in Example 8, Steps 1-2, for 4-[(5-ethyl-2-thien-3-ylthieno[3,2-c]isoquinolin-4(H)-yl)sulfonyl]phenol.

$^1$H NMR δ 0.92 (m, 3H, CH$_2$CH$_3$), 1.49 (m, 2H, CH$_2$CH$_3$), 5.12 (m, 1H, CHCH$_2$), 6.45 (d, J=9 Hz, 2H, ArH), 7.06-7.16 (overlapping m, 5H, ArH), 7.23 (m, 1H, ArH), 7.36 (m, 1H, ArH), 7.46 (m, 2H, ArH), 7.65 (s, 1H, ArH), 7.74 (d, J=8 Hz, 2H, ArH), 10.3 (s, 1H, ArOH). MS (ESI) m/z 446 [M−HR]$^−$ Analysis calc. for C$_{25}$H$_{21}$NO$_3$S$_2$: C, 67.09; H, 4.73; N, 3.13. Found: C, 67.09; H, 5.03; N, 3.08.

EXAMPLE 12 and EXAMPLE 13

2-Bromo-4-[(2-bromo-5-methylthieno[3,2-c]isoquinolin-4(5H)-yl)sulfonyl]phenol and 2,6-Dibromo-4-[(2-bromo-5-methylthieno[3,2-c]isoquinolin-4(5H)-yl)sulfonyl]phenol Starting from 4-[(5-Methylthieno[3,2-c]isoquinolin4(H)-yl)sulfonyl]phenol (0.72 g, 2.0 mmol) and N-bromosuccinimide (0.78 g, 4.4 mmol, 2.2 eq), the title compounds were synthesized in essentially the same manner as described in Example 6 for 4-[(2-Bromo-5-methylthieno[3,2-c]isoquinolin4(H)-yl)sulfonyl]phenol.

2-Bromo-4-[(2-bromo-5-methylthieno[3,2-c]isoquinolin-4(5H)-yl)sulfonyl]phenol Yield: 0.23 g white solid, 22%. $^1$H NMR δ 1.21 (d, J=7 Hz, 3H, CHCH$_3$), 5.40 (m, 1H, CHCH$_3$), 6.61 (d, J=9 Hz, 1H, ArH), 7.00 (d, J=8 Hz, 1H, ArH), 7.02 (m, 1H, ArH), 7.10 (m, 1H, ArH), 7.16 (m, 1H, ArH), 7.25-7.26 (overlapping s, d, 2H, ArH), 7.34 (s, 1H, ArH), 11.2 (broad s, 1H, ArOH). MS (ESI) m/z 512 [M–H]$^-$ Analysis calc. for C$_{18}$H$_{13}$Br$_2$NO$_3$S$_2$: C, 41.96; H, 2.54; N, 2.72. Found: C, 41.98; H, 2.71; N, 2.51.

2,6-Dibromo-4-[(2-bromo-5-methylthieno[3,2-c]isoquinolin-4(5H)-yl)sulfonyl]phenol Yield: 0.34 g white solid, 29% (based on conversion of starting material). $^1$H NMR δ 1.18 (d, J=7 Hz, 3H, CHCH$_3$), 5.32 (m, 1H, CHCH$_3$), 7.01-7.03 (overlapping s, d, 3H, ArH), 7.10 (m, 1H, ArH), 7.17 (m, 1H, ArH), 7.25 (d, J=8 Hz, 1H, ArH), 7.29 (s, 1H, ArH). MS (ESI) m/z 590 [M–H]$^-$ Analysis calc. for C$_{18}$H$_{12}$Br$_3$NO$_3$S$_2$: C, 36.39; H, 2.04; N, 2.36. Found: C, 36.36; H, 2.31; N, 2.12.

EXAMPLE 14

4-[(2-Formyl-5-ethylthieno[3,2-c]isoquinolin-4(5H)-yl)sulfonyl]phenol

Step 1: 5-Ethyl-4-[(4-methoxyphenyl)sulfonyl]-4,5-dihydrothieno[3,2-c]isoquinoline-2-carbaldehyde (Compound 13)

A solution of 2-bromo-4-[(4-methoxyphenyl)sulfonyl]-5-ethyl-4,5-dihydrothieno[3,2-c]isoquinoline (2.3 g, 5.0 mmol) in dry tetrahydrofuran (45 mL) was cooled to –78° C. and treated with a solution of butyllithium in hexanes (1.35 M, 3.7 mL, 5.0 mmol) during ca. 2 min followed immediately by the fast addition of dry dimethylformamide (1.9 mL, 25 mmol). After 30 min further at –78° C., the reaction was quenched with 10% aqueous ammonium chloride (100 mL) and extracted with ethyl acetate (3×50 mL). The combined extracts were washed with brine (75 mL), dried (MgSO$_4$), and concentrated in vacuo to give the crude product as a light orange solid (2.0 g) which was taken up in methylene chloride (ca. 8 ML) and pre-adsorbed on silica gel (8 g). Flash chromatography on silica gel (72 g) eluting 50-, then 75% methylene chloride-hexane, and then methylene chloride gave the title compound (1.7 g, 81%, m.p. 129-32° C.) as a pale yellow solid.

$^1$H NMR δ 0.92 (m, 3H, CH$_2$CH$_3$), 1.44 (m, 2H, CH$_2$CH$_3$), 3.63 (s, 3H, OCH$_3$), 5.20 (m, 1H, CHCH$_2$), 6.66 (d, J=9 Hz, 2H, ArH), 7.14-7.20 (overlapping m, 3H, ArH), 7.23 (d, J=8 Hz, 1H, ArH), 7.26 (m, 1H, ArH), 7.31 (d, J=8 Hz, 1H, ArH), 8.18 (s, 1H, ArH), 9.99 (s, 1H, CHO). MS (EI) m/z 413 [M]$^+$ Analysis calc. for C$_{21}$H$_{19}$NO$_4$S$_2$: C, 61.00: H, 4.63; N, 3.39. Found: C, 60.61; H, 4.73; N, 3.27.

Step 2: 5-Ethyl-4-[(4-methoxyphenyl)sulfonyl]-2-vinyl-4,5-dihydrothieno[3,2-c]isoquinoline (Compound 16)

A suspension of methyltriphenylphosphonium bromide (2.30 g, 6.44 mmol) in dry tetrahydrofuran (16 mL) was treated dropwise with a pentane solution of t-butyllithium (1.0 M, 3.9 mL, 3.9 mmol) at 0° C. during several min. After the addition was complete, the suspension was warmed to 23° C. and after a further 10 min, a solution of 5-ethyl-4-[(4-methoxyphenyl)sulfonyl]-4,5-dihydrothieno[3,2-c]isoquinoline-2-carbaldehyde (1.33 g, 3.22 mmol) in dry tetrahydrofuran (16 mL+8 mL wash) was added. After a further 15 min, the reaction was quenched with water (160 mL) and extracted with ethyl acetate (160 mL). The extract was washed with brine (160 mL), dried (Na$_2$SO$_4$), and concentrated in vacuo to give the crude product as an orange solid (2.46 g). Flash chromatography on silica gel (24 g) eluting 25-, and then 50% methylene chloride-hexane gave the title compound (1.20 g, 90%, m.p. 131-33° C.) as a pale yellow solid.

$^1$H NMR δ 0.90 (m, 3H, CH$_2$CH$_3$), 1.43 (m, 2H, CH$_2$CH$_3$), 3.63 (s, 3H, OCH$_3$), 5.11 (m, 1H, CHCH$_2$), 5.26 (d, J=11 Hz, 1H, CHH=), 5.61 (d, J=17 Hz, 1H, CHH=), 6.66 (d, J=9 Hz, 2H, ArH), 6.93-7.00 (overlapping m, 2H, ArCH=, ArH), 7.07-7.14 (overlapping m, 2H, ArH), 7.17 (d, J=9 Hz, 2H, ArH), 7.21 (d, J=7 Hz, 1H, ArH), 7.29 (s, 1H, ArH). MS (EI) m/z 411 [M]$^+$ Analysis calc. for C$_{22}$H$_{21}$NO$_3$S$_2$: C, 64.21; H, 5.14; N, 3.40. Found: C. 63.85: H. 5.25: N, 3.31.

Step 3: 2,5-Diethyl-4-[(4-methoxyphenyl)sulfonyl]-4,5-dihydrothieno[3,2-c]isoquinoline (Compound 16)

A solution of 5-ethyl-4-[(4-methoxyphenyl)sulfonyl]-2-vinyl4,5-dihydrothieno[3,2-c]isoquinoline (1.44 g, 3.50 mmol) in ethyl acetate (35 mL) was hydrogenated over 10% palladium-on-carbon (0.29 g) at 23° C. and 1 atm. After 1 h the catalyst was filtered (Celite), washed with ethyl acetate (35 mL), and the filtrate was concentrated in vacuo to give the crude product (1.37 g) as a pale yellow solid. Recrystallization from boiling hexane provided the title compound (1.26 g, 87%, m.p. 105.0-105.5° C.) as shiny pale yellow needles.

$^1$H NMR δ 0.89 (m, 3H, CH$_2$CH$_3$), 1.28 (m, 3H, CH$_2$CH$_3$), 1.41 (m, 2H, CH$_2$CH$_3$), 2.86 (m, 2H, CH$_2$CH$_3$), 3.62 (s, 3H, OCH$_3$), 5.07 (m, 1H, CHCH$_2$), 6.65 (d, J=9 Hz, 2H, ArH), 6.92 (m, 1H, ArH), 7.01 (s, 1H, ArH), 7.03-7.09 (overlapping m, 2H, ArH), 7.14 (d, J=9 Hz, 2H, ArH), 7.17 (m, 1H, ArH). MS (ESI) m/z 414 [M+H]$^+$ Analysis calc. for C$_{22}$H$_{23}$NO$_3$S$_2$: C, 63.90; H, 5.61; N, 3.39. Found: C, 63.78; H, 5.52; N, 3.31.

Step 4: 4-[(2,5-Diethylthieno[3,2-c]isoquinolin-4(5H)-yl)sulfonyl]phenol (Compound 17)

Starting from 2,5-diethyl-4-[(4-methoxyphenyl)sulfonyl] 4,5-dihydrothieno[3,2-c]isoquinoline (1.26 g, 3.05 mmol) in place of 2-bromo-4-[(4-methoxyphenyl)sulfonyl]-5-methyl4,5-dihydrothieno[3,2-c]isoquinoline, the title compound (0.87 g, 71%, m.p. 119-122° C.) was synthesized in essentially the same manner as described in Example 6, Method B, Step 2.

$^1$H NMR δ 0.89 (m, 3H, CH$_2$CH$_3$), 1.28 (m, 3H, CH$_2$CH$_3$), 1.41 (m, 2H, CH$_2$CH$_3$), 2.85 (m, 2H, CH$_2$CH$_3$), 5.05 (m, 1H, CHCH$_2$), 6.44 (d, J=9 Hz, 2H, ArH), 6.94 (m, 1H, ArH), 7.00

(s, 1H, ArH), 7.04 (d, J=9 Hz, 2H, ArH), 7.06-7.08 (overlapping m, 2H, ArH), 7.17 (m, 1H, ArH), 10.2 (s, 1H, ArOH). MS (ESI) m/z 400 [M+H]$^+$ Analysis calc. for $C_{21}H_{21}NO_3S_2$: C. 63.13; H. 5.30: N, 3.51. Found: C. 62.86: H. 5.48: N, 3.14.

EXAMPLE 15

In Vitro Methods

NFκB-Luciferase, IL-6 and Creatine Kinase Assays

Cells

T-175 flasks of 100% confluent HAECT-1 cells (immortalized human aortic endothelial cells) were washed with 8 ml of HBSS (HEPES buffered saline solution) and infected for four hours with 6 ml of a 1:10 dilution of Ad5-wt-hER virus (an adenovirus transfection vector that mediates CMV promoter driven expression of human ER) in phenol red free Endothelial Cell Basal medium (Clonetics, San Diego Calif., Catalog # CC-3129) containing 0.25% bovine serum albumin (EBM-BSA). After four hours, cells were washed with EBM-BSA and incubated overnight in the same medium. Following overnight incubation, cells were washed with EBM-BSA and infected for 2 hours with 6 ml of a 1:10 dilution of Ad5-3×(NF B).Luc virus (Adenovirus luciferase expression vector driven by 3 repeats of the MHC NF b site 5' to the thymidine kinase promoter) in EBM-BSA. After two hours, cells were washed and incubated at 34° C. for 1 hour. Cells were then washed, trypsinized, counted and resuspended in 95% FBS/5% dimethylsulfoxide at a concentration of 4×10$^6$ cells/ml, frozen as 1 or 5 ml aliquots in cryo-vials and stored at −150° C. Control (no ER infection) cells were processed as above without Ad5-wt-hER virus infection.

Assays

ER infected HAECT-1 cells or control cells were thawed, diluted 42× in warm EBM-BSA, plated into 96-well plates at 0.1 ml/well and incubated for 4 h at 34° C. Test compounds were added to the cells as 2× stocks in EBM-BSA containing 2 ng/ml IL-1 (R&D Systems) and plates were returned to the incubator (34° C.). After 15-20 h, 100 l aliquots of media were removed from the cells and assayed for IL-6 content using a BioSource human IL-6 ELISA Kit. Cells were subsequently washed with 300 l of Dulbecco's phosphate buffered saline and lysed in 50 l of Cell Culture Lysis Reagent (Promega). Luciferase was determined on a Wallac Victor$^2$ Luminometer (Gaithersburg, Md.) using 10 l of lysate and mixing with 100 l of Promega Luciferase Assay reagent. Creatine kinase was determined from the rate of increase in $A_{340}$ following addition of 100 l of CK assay reagent (Sigma, cat. No 47-10) to the remainder of the cell lysate.

IL-6 Promoter Luciferase Assay

HAECT-1 cells (immortalized human aortic endothelial cells) in 96-well plates were infected for two hours with 50 l/well of a 1:10 dilution of Ad5-wt-hER virus in EBM-BSA. After two hours, virus was removed, 100 l of EBM-BSA was added per well. Following overnight incubation, EBM-BSA was removed and cells were infected for 2 hours with 50 l/well of a 1:10 dilution of Ad5-IL6(1250 bp).Luc virus (Adenovirus luciferase expression vector driven by a 1250 bp section of the human IL-6 promoter 5' to the thymidine kinase promoter) in EBM-BSA. After two hours, virus was removed and plates were incubated at 34° C. for 1-2 h. Cells were subsequently treated with test compounds/IL-1 and luciferase activity was determined as above.

Data Analyses

For IC$_{50}$ and EC$_{50}$ calculations, mean IL-6, luciferase or CK values versus log10 of the compound concentration were fitted to a four parameter logistic equation. The IC$_{50}$/EC$_{50}$ value, 'Hill slope', upper and lower limits of the curve were iteratively estimated.

Mice

Ovariectomized C57BL/6 mice (16-20 g) (Taconic) were separated into groups of 8. After 5-7 days of recuperation, the mice were fed a chow diet or an atherogenic diet (15.75% fat, 1.25% cholesterol and 0.5% sodium cholate) (Purina diet #21539). EE or test compound was administered once daily by gavage in a methylcellulose/tween vehicle (0.1 ml per mouse) for 5 weeks. At the end of the experimental period, the liver was collected and uterine wet weight was recorded.

RNA Analysis

Liver total RNA was prepared by using Trizol reagent (BRL). Estrogen and compound regulation of NF-B target genes were verified by real time RT-PCR using an ABI PRISM 7700 Sequence Detection System according to the manufacturer's protocol (Applied Biosystems). The data was analyzed using the Sequence Detector v1.7 software (Applied Biosystems) and normalized to GAPDH using the Applied Biosystems primer set.

In vitro Results

Table 1 summarizes the activities of compounds contained herein in the HAECT-1 NF-κB, IL-6 and creatine kinase assays in Ad5-wt-ER infected cells and is compared to activities of the same compounds in the HAECT-1 NF-κB and creatine kinase assays in uninfected cells.

TABLE 1

Effects of 17-β-estradiol on NF-κB. IL-6 and CK expression in Ad5-wt-ER infected HAECT-1 cells

| Example # | ER/NF-KB-luc | | ER/IL-6 | | ER/CK | |
|---|---|---|---|---|---|---|
| | IC$_{50}$ (nM) | % Eff* | IC$_{50}$ (nM) | % Eff | EC$_{50}$ (nM) | % Eff* |
| E2 | 1 | 100 | 1.7 | 100 | 5.8 | 100 |
| 4 | | | 66.8 | 172 | 100 | 42 |
| 5 | | | 21.3 | 174 | N/O | |
| 6 | | | 28.2 | 162 | N/O | |
| 7 | 1451 | 84 | 5822 | 161 | N/O | |
| 8 | 19 | 92 | 8.9 | 164 | N/O | |
| 9 | | | 7.7 | 194 | 47 | 33 |
| 10 | | | | | | |
| 11 | | | 24.6 | 132 | 15 | 63 |
| 12 | | | 1475 | 197 | 1543 | 35 |
| 13 | | | | | | |

N/O - activity not observed at doses tested.
*Efficacy values are relative to the maximal inhibition (NF-κB or IL-6 assay) or stimulation (CK assay) observed with E2

E2 inhibits NF-κB and IL-6 expression in Ad5-wt-ER infected HAECT-1 cells with an IC$_{50}$ value around 1 nM and induces expression of creatine kinase in the same cells with similar potency (5.8 nM). In contrast, compounds of the present invention potently and efficaciously inhibit NF-κB and IL-6 expression in Ad5-wt-ER infected HAECT-1 cells show little or no CK expression (Table 1) in an ER-dependent manner. The ability of compounds of the present invention to inhibit NF-κB and IL-6 expression without inducing CK activity (Table 1) is consistent with an anti-inflammatory activity in the absence of classic estrogenic activity.

Evaluation of Test Compound Using an ERE-Reporter Test Procedure in MCF-7 Breast Cancer Cells Stock solutions of test compounds (usually 0.1 M) are prepared in d then diluted 10 to 100-fold with DMSO to make working solutions of 1 or 10 mM. The DMSO stocks are stored at either 4° C. (0.1 M) or −20° C. (<0.1 M). MCF-7 cells are passaged twice a week with growth medium [D-MEM/F-12 medium containing 10% (v/v) heat-inactivated fetal bovine serum. 1% (v/v) Penicillin-Streptomycin, and 2 mM glutaMax-1]. The cells are maintained in vented flasks at 37° C. inside a 5% $CO_2$/95% humidified air incubator. One day prior to treatment, the cells are plated with growth medium at 25,000 cells/well into 96 well plates and incubated at 37° C. overnight.

The cells are infected for 2 hr at 37° C. with 50 µl/well of a 1:10 dilution of adenovirus 5-ERE-tk-luciferase in experimental medium [phenol red-free D-MEM/F-12 medium containing 10% (v/v) heat-inactived charcoal-stripped fetal bovine serum, 1% (v/v) Penicillin-Streptomycin, 2 mM glutaMax-1, 1 mM sodium pyruvate]. The wells are then washed once with 150 µl of experimental medium. Finally, the cells are treated for 24 hr at 37° C. in replicates of 8 wells/treatment with 150 µl/well of vehicle ($\leq$0.1% v/v DMSO) or compound that is diluted $\geq$1000-fold into experimental medium.

Initial screening of test compounds is done at a single dose of 1 µM that is tested alone (estrogen receptor agonist mode) or in combination with 0.1 nM 17β-estradiol ($EC_{80}$; estrogen receptor antagonist mode). Each 96 well plate also includes a vehicle control group (0.1% v/v DMSO) and an estrogen receptor agonist control group (either 0.1 or 1 nM 17β-estradiol). Dose-response experiments are performed in either the estrogen receptor agonist and/or estrogen receptor antagonist modes on active compounds in log increases from $10^{-14}$ to $10^{-5}$ M. From these dose-response curves, $EC_{50}$ and $IC_{50}$ values, respectively, are generated. The final well in each treatment group contains 5 µl of $3 \times 10^{-5}$ M ICI-182,780 ($10^{-6}$ M final concentration) as an estrogen receptor antagonist control.

After treatment, the cells are lysed on a shaker for 15 min with 25 µl/well of 1× cell culture lysis reagent (Promega Corporation). The cell lysates (20 µl) are transferred to a 96 well luminometer plate, and luciferase activity is measured in a MicroLumat LB 96 P luminometer (EG & G Berthold) using 100 µl/well of luciferase substrate (Promega Corporation). Prior to the injection of substrate, a 1 second background measurement is made for each well. Following the injection of substrate, luciferase activity is measured for 10 seconds after a 1 second delay. The data are transferred from the luminometer to a Macintosh personal computer and analyzed using the JMP software (SAS Institute); this program subtracts the background reading from the luciferase measurement for each well and then determines the mean and standard deviation of each treatment.

The luciferase data are transformed by logarithms, and the Huber M-estimator is used to down-weight the outlying transformed observations. The JMP software is used to analyze the transformed and weighted data for one-way ANOVA (Dunnett's test). The compound treatments are compared to the vehicle control results in the estrogen receptor agonist mode, or the positive estrogen receptor agonist control results (0.1 nM 17β-estradiol) in the estrogen receptor antagonist mode. For the initial single dose experiment, if the compound treatment results are significantly different from the appropriate control (p<0.05), then the results are reported as the percent relative to the 17β-estradiol control [i.e., ((compound—vehicle control)/(17β-estradiol control—vehicle control))× 100)]. The JMP software is also used to determine the $EC_{50}$ and/or $IC_{50}$ values from the non-linear dose-response curves.

Evaluation of Uterotrophic Activity

Uterotrophic activity of a test compound can be measured according to the following standard pharmacological test procedures.

Procedure 1: Sexually immature (18 days of age) Sprague-Dawley rats are obtained from Taconic and provided unrestricted access to a casein-based diet (Purina Mills 5K96C) and water. On day 19, 20 and 21 the rats are dosed subcutaneously with 17α-ethinyl-17β-estradiol (0.06 µg/rat/day), test compound or vehicle (50% DMSO/50% Dulbecco's PBS). To assess estrogen receptor antagonist, compounds are coadministered with 17α-ethinyl-17β-estradiol (0.06 µg/rat/day). There are six rats/group and they are euthanized approximately 24 hours after the last injection by $CO_2$ asphyxiation and pneumothorax. Uteri are removed and weighed after trimming associated fat and expressing any internal fluid. A tissue sample can also be snap frozen for analysis of gene expression (e.g. complement factor 3 mRNA).

Procedure 2: Sexually immature (18 days of age) 129 SvE mice are obtained from Taconic and provided unrestricted access to a casein-based diet (Purina Mills 5K96C) and water. On day 22, 23, 24 and 25 the mice are dosed subcutaneously with compound or vehicle (corn oil). There are six mice/group and they are euthanized approximately 6 hours after the last injection by $CO_2$ asphyxiation and pneumothorax. Uteri are removed and weighed after trimming associated fat and expressing any internal fluid.

Evaluation of Osteoporosis and Lipid Modulation (Cardioprotection)

Female Sprague-Dawley rats, ovariectomized or sham operated, are obtained 1 day after surgery from Taconic Farms (weight range 240-275 g). They are housed 3 or 4 rats/cage in a room on a 12/12 (light/dark) schedule and provided with food (Purina 5K96C rat chow) and water ad libitum. Treatment for all studies begin 1 day after arrival and rats are dosed 7 days per week as indicated for 6 weeks. A group of age matched sham operated rats not receiving any treatment serve as an intact, estrogen replete control group for each study.

All test compounds are prepared in a vehicle of 50% DMSO (JT Baker, Phillipsburg, N.J.)/1× Dulbecco's phosphate saline (GibcoBRL, Grand Island, N.Y.) at defined concentrations so that the treatment volume is 0.1 mL/100 g body weight. 17β-estradiol is dissolved in corn oil (20 µg/mL) and delivered subcutaneously, 0.1 mL/rat. All dosages are adjusted at three week intervals according to group mean body weight measurements, and given subcutaneously.

Five weeks after the initiation of treatment and one week prior to the termination of the study, each rat is evaluated for bone mineral density (BMD). The total and trabecular density of the proximal tibia are evaluated in anesthetized rats using an XCT-960M (pQCT; Stratec Medizintechnik, Pforzheim, Germany). The measurements are performed as follows: Fifteen minutes prior to scanning, each rat is anesthetized with an intraperitoneal injection of 45 mg/kg ketamine, 8.5 mg/kg xylazine, and 1.5 mg/kg acepromazine.

The right hind limb is passed through a polycarbonate tube with a diameter of 25 mm and taped to an acrylic frame with the ankle joint at a 90° angle and the knee joint at 180°. The polycarbonate tube is affixed to a sliding platform that maintains it perpendicular to the aperture of the pQCT. The platform is adjusted so that the distal end of the femur and the proximal end of the tibia is in the scanning field. A two dimensional scout view is run for a length of 10 mm and a line resolution of 0.2 mm. After the scout view is displayed on the monitor, the proximal end of the tibia is located. The pQCT scan is initiated 3.4 mm distal from this point. The pQCT scan is 1 mm thick, has a voxel (three dimensional pixel) size of 0.140 mm, and consists of 145 projections through the slice.

After the pQCT scan is completed, the image is displayed on the monitor. A region of interest including the tibia but excluding the fibula is outlined. The soft tissue is mathematically removed using an iterative algorithm. The density of the remaining bone (total density) is reported in $mg/cm^3$. The outer 55% of the bone is mathematically peeled away in a concentric spiral. The density of the remaining bone (Trabecular density) is reported in $mg/cm^3$.

One week after BMD evaluation the rats are euthanized by $CO_2$ asphyxiation and pneumothorax, and blood is collected for cholesterol determination. The uteri are also removed and the weighed after trimming associated fat and expressing any luminal fluid. Total cholesterol is determined using a Boehringer-Mannheim Hitachi 911 clinical analyzer using the Cholesterol/HP kit. Statistics were compared using one-way analysis of variance with Dunnet's test.

Evaluation of Antioxidant Activity

Porcine aortas are obtained from an abattoir, washed, transported in chilled PBS, and aortic endothelial cells are harvested. To harvest the cells, the intercostal vessels of the aorta are tied off and one end of the aorta clamped. Fresh, sterile filtered, 0.2% collagenase (Sigma Type I) is placed in the vessel and the other end of the vessel then clamped to form a closed system. The aorta is incubated at 37° C. for 15-20 minutes, after which the collagenase solution is collected and centrifuged for 5 minutes at 2000×g. Each pellet is suspended in 7 mL of endothelial cell culture medium consisting of phenol red free DMEM/Ham's F12 media supplemented with charcoal stripped FBS (5%), NuSerum (5%), L-glutamine (4 mM), penicillin-streptomycin (1000 U/ml, 100 μg/ml) and gentamycin (75 μg/ml), seeded in 100 mm petri dish and incubated at 37° C. in 5% $CO_2$. After 20 minutes, the cells are rinsed with PBS and fresh medium added, this was repeated again at 24 hours. The cells are confluent after approximately 1 week. The endothelial cells are routinely fed twice a week and, when confluent, trypsinized and seeded at a 1:7 ratio. Cell mediated oxidation of 12.5 μg/mL LDL is allowed to proceed in the presence of the compound to be evaluated (5 μM) for 4 hours at 37° C. Results are expressed as the percent inhibition of the oxidative process as measured by the TBARS (thiobarbituric acid reactive substances) method for analysis of free aldehydes [Yagi, Biochemical Medicine 15: 212-6 (1976)].

Progesterone Receptor mRNA Regulation Standard Pharmacological Test Procedure

This test procedure can be used to evaluate the estrogenic or antiestrogenic activity of compounds from this invention [Shughrue, et al., Endocrinology 138: 5476-5484 (1997)].

Rat Hot Flush Test Procedure

The effect of test compounds on hot flushes can be evaluated in a standard pharmacological test procedure which measures the ability of a test compound to blunt the increase in tail skin temperature which occurs as morphine-addicted rats are acutely withdrawn from the drug using naloxone [Merchenthaler, et al., Maturitas 30: 307-16 (1998)]. It can also be used to detect estrogen receptor antagonist activity by co-dosing test compound with the reference estrogen.

Evaluation of Vasomotor Function in Isolated Rat Aortic Rings

Sprague-Dawley rats (240-260 grams) are divided into 4 groups:
1. Normal non-ovariectomized (intact)
2. Ovariectomized (ovex) vehicle treated
3. Ovariectomized 17β-estradiol treated (1 mg/kg/day)
4. Ovariectomized animals treated with test compound (various doses)

Animals are ovariectomized approximately 3 weeks prior to treatment. Each animal receives either 17-β estradiol sulfate (1 mg/kg/day) or test compound suspended in distilled, deionized water with 1% tween-80 by gastric gavage. Vehicle treated animals received an appropriate volume of the vehicle used in the drug treated groups.

Animals are euthanized by $CO_2$ inhalation and exsanguination. Thoracic aortae are rapidly removed and placed in 37° C. physiological solution with the following composition (mM): NaCl (54.7), KCl (5.0), $NaHCO_3$ (25.0), $MgCl_2$ $2H_2O$ (2.5), D-glucose (11.8) and $CaCl_2$ (0.2) gassed with $CO_2$—$O_2$, 95%/5% for a final pH of 7.4. The advantitia is removed from the outer surface and the vessel is cut into 2-3 mm wide rings. Rings are suspended in a 10 mL tissue bath with one end attached to the bottom of the bath and the other to a force transducer. A resting tension of 1 gram is placed on the rings. Rings are equilibrated for 1 hour, signals are acquired and analyzed.

After equilibration, the rings are exposed to increasing concentrations of phenylephrine ($10^{-8}$ to $10^{-4}$M) and the tension recorded. Baths are then rinsed 3 times with fresh buffer. After washout, 200 mM L-NAME is added to the tissue bath and equilibrated for 30 minutes. The phenylephrine concentration response curve is then repeated.

Evaluation of Cardioprotective Activity

Apolipoprotein E-deficient C57/B1J (apo E KO) mice are obtained from Taconic Farms. All animal procedures are performed under strict compliance to IACUC guidelines. Ovariectomized female apo E KO mice, 4-7 weeks of age, are housed in shoe-box cages and were allowed free access to food and water. The animals are randomized by weight into groups (n=12-15 mice per group). The animals are dosed with test compounds or estrogen (17β-estradiol sulfate at 1 mg/kg/day) in the diet using a Precise-dosing Protocol, where the amount of diet consumed is measured weekly, and the dose adjusted accordingly, based on animal weight. The diet used is a Western-style diet (57U5) that is prepared by Purina and contains 0.50% cholesterol, 20% lard and 25 IU/KG Vitamin E. The animals are dosed/fed using this paradigm for a period of 12 weeks. Control animals are fed the Western-style diet and receive no compound. At the end of the study period, the animals are euthanized and plasma samples obtained. The hearts are perfused in situ, first with saline and then with neutral buffered 10% formalin solution.

For the determination of plasma lipids and lipoproteins, total cholesterol and triglycerides are determined using enzymatic methods with commercially available kits from Boehringer Mannheim and Wako Biochemicals, respectively and analyzed using the Boehringer Mannheim Hitachii 911 Analyzer. Separation and quantification of plasma lipoproteins were performed using FPLC size fractionation. Briefly, 50-100 mL of serum is filtered and injected into Superose 12 and Superose 6 columns connected in series and eluted at a constant flow rate with 1 mM sodium EDTA and 0.15 M NaCl. Areas of each curve representing VLDL. LDL and HDL are integrated using Waters Millennium™ software, and each lipoprotein fraction is quantified by multiplying the Total Cholesterol value by the relative percent area of each respective chromatogram peak.

For the quantification of aortic atherosclerosis, the aortas are carefully isolated and placed in formalin fixative for 48-72 hours before handling. Atherosclerotic lesions are identified using Oil Red O staining. The vessels are briefly destained, and then imaged using a Nikon SMU800 microscope fitted with a Sony 3CCD video camera system in concert with IMAQ Configuration Utility (National Instrument) as the image capturing software. The lesions are quantified en face along the aortic arch using a custom threshold utility software package (Coleman Technologies). Automated lesion assessment is performed on the vessels using the threshold function of the program, specifically on the region contained within the aortic arch from the proximal edge of the brachio-cephalic trunk to the distal edge of the left subclavian artery. Aortic atherosclerosis data are expressed as percent lesion involvement strictly within this defined luminal area.

Evaluation of Cognition Enhancement

Ovariectomized rats (n=50) are habituated to an 8-arm radial arm maze for 10-min periods on each of 5 consecutive days. Animals are water-deprived prior to habituation and testing. A 100 µL aliquot of water placed at the ends of each arm serves as reinforcement. Acquisition of a win-shift task in the radial arm maze is accomplished by allowing the animal to have access to one baited arm. After drinking, the animal exits the arm and re-enters the central compartment, where it now has access to the previously visited arm or to a novel arm. A correct response is recorded when the animal chooses to enter a novel arm. Each animal is given 5 trials per day for 3 days. After the last acquisition trial, the animals are assigned to one of the following 4 groups:

1. Negative controls: injected with 10% DMSO/sesame oil vehicle once daily for 6 days (1 mL/kg, SC)
2. Positive controls: injected with 17β-estradiol benzoate for 2 days and tested 4 days after the second injection (17β-estradiol benzoate at 10 µg/0.1 mL per rat)
3. Estradiol: 17β-estradiol will be injected daily for 6 days (20 µg/kg, SC)
4. Test compound: injected daily for 6 days (doses vary).

All injections will begin after testing on the last day of acquisition. The last injection for groups 1, 3, and 4 will take place 2 hours before testing for working memory.

The test for working memory is a delayed non-matching-to-sample task (DNMS) utilizing delays of 15, 30, or 60 seconds. This task is a variation of the acquisition task in which the rat is placed in the central arena and allowed to enter one arm as before. A second arm is opened once the rat traverses halfway down the first arm, and again the rat is required to choose this arm. When it has traveled halfway down this second arm, both doors are closed and the delay is instituted. Once the delay has expired, both of the original two doors, and a third novel door, are opened simultaneously. A correct response is recorded when the animal travels halfway down the third, novel arm. An incorrect response is recorded when the animal travels halfway down either the first or second arms. Each animal will receive 5 trials at each of the three delay intervals for a total of 15 trials per subject.

Evaluation of Effect on Pleurisy

The ability to reduce the symptoms of experimentally-induced pleurisy in rats can be evaluated according to the procedure of Cuzzocrea [Endocrinology 141: 1455-63 (2000)].

Evaluation of Protection Against Glutamate-Induced Cytotoxicity (Neuroprotection)

The neuroprotective activity of compounds of this invention can be evaluated in an in vitro standard pharmacological test procedure using glutamate challenge [Zaulyanov, et al., Cellular & Molecular Neurobiology 19: 705-18 (1999); Prokai, et al., Journal of Medicinal Chemistry 44: 110-4 (2001)].

Evaluation in the Mammary End Bud Test Procedure

Estrogens are required for full ductal elongation and branching of the mammary ducts, and the subsequent development of lobulo-alveolar end buds under the influence of progesterone. In this test procedure, the mammotrophic activity of selected compounds of the invention can be evaluated according to the following standard pharmacological test procedure. Twenty-eight day old Sprague-Dawley rats (Taconic Farms, Germantown, N.Y.) are ovariectomized and rested for nine days. Animals are housed under a 12-hour light/dark cycle, fed a casein-based Purina Laboratory Rodent Diet 5K96 (Purina, Richmond, Ind.) and allowed free access to water. Rats were then dosed subcutaneously for six days with vehicle (50% DMSO (JT Baker, Phillipsburg, N.J.)/50% 1× Dulbecco's Phosphate buffered saline (GibcoBRL, Grand Island, N.Y.), 17β-estradiol (0.1 mg/kg) or test compound (20 mg/kg). For the final three days, rats are also dosed subcutaneously with progesterone (30 mg/kg). On the seventh day, rats are euthanised and a mammary fat pad excised. This fat pad is analyzed for casein kinase II mRNA as a marker of end bud proliferation. Casein kinase II mRNA is anlayzed by real-time RT-PCR. Briefly, RNA is isolated following Trizol (GibcoBRL, Grand Island, N.Y.) according to the manufacture's directions, Samples are treated with DNAse I using DNA-free kit (Ambion), and casein kinase II mRNA levels are measured by real-time RT-PCR using the Taqman Gold procedure (PE Applied Biosystems). A total of 50 ng of RNA is analyzed in triplicate using casein kinase II specific primer pair (5' primer, CACACGGATGGCGCATACT (SEQ ID No: 1); 3' primer, CTCGGGATGCACCATGAAG (SEQ ID No: 2)) and customized probe (TAMRA-CGGCACTGGTTTC-CCTCACATGCT-FAM (SEQ ID No. 3)). Casein kinase II mRNA levels are normalized to 18s ribosomal RNA contained within each sample reaction using primers and probe supplied by PE Applied Biosystems.

Evaluation in the HLA Rat Standard Pharmacological Test Procedure for Inflammatory Bowel Disease Representative compounds can be evaluated in the HLA rat standard pharmacological test procedure which emulates inflammatory bowel disease in humans. The following briefly describes the procedure used and results obtained. Male HLA-B27 rats are obtained from Taconic and provided unrestricted access to food (PMI Lab diet 5001) and water. Rats are dosed subcutaneously once per day with either vehicle (50% DMSO/50% 1× Dulbecco's Phosphate Buffered Saline) or test compound (0.1 to 10 mg/kg) for at least one week. Stool quality is observed daily and graded according to the following scale: Diarrhea=3; soft stool=2; normal stool=1. At the end of the study, serum is collected and stored at −70° C. A section of colon is prepared for histological analysis and an additional segment is analyzed for myeloperoxidase activity.

For histological analysis, colonic tissue is immersed in 10% neutral buffered formalin. Each specimen of colon is separated into four samples for evaluation. The formalin-fixed tissues are processed in a Tissue Tek vacuum infiltration processor (Miles, Inc; West Haven, Conn.) for paraffin embedding. The samples are sectioned at 5 µm and then stained with hematoxylin and eosin (H&E) for blinded histologic evaluations using a scale modified after Boughton-Smith. After the scores are completed the samples are unblinded, and data are tabulated and analyzed by ANOVA linear modeling with multiple mean comparisons. Sections of colonic tissue are evaluated for several disease indicators and given relative scores.

Evaluation in Three Models of Arthritis

Lewis rat assay of adjuvant-induced arthritis. Sixty, female, 12 weeks old, Lewis rats are housed according to standard facility operating procedures. They receive a standard regimen of food and water ad libitum. Each animal is identified by a cage card indicating the project group and animal number. Each rat number is marked by indelible ink marker on the tail. At least 10-21 days before study they are anesthetized and ovariectomized by standard aseptic surgical techniques.

Freund's Adjuvant-Complete (Sigma Immuno Chemicals, St. Louis, Mo.) is used to induce arthritis, each mL containing 1 mg Mycobacterium tuberculosis heat killed and dried, 0.85 mL mineral oil and 0.15 mL mannide monooleate Lot No. 084H8800.

The following are examples of two test procedures. Inhibition test procedure: Thirty rats are injected intradermally with 0.1 mL of Freund's Adjuvant-Complete at the base of the tail. The animals are randomized to four groups, each group containing six rats. Each day, the groups receive vehicle (50% DMSO (J T Baker, Phillipsburg, N.J/)/1× Dulbecco's phosphate saline (GibcoBRL, Grand Island, N.Y.)) or test compound (0.1-10 mg/kg, administered subcutaneously). All rats begin treatment on Day 1.

Treatment test procedure: Thirty rats are injected intradermally with 0.1 mL of Freund's Adjuvant-Complete at the base of the tail. The animals are randomized to four groups, each group containing six rats. Each day, the groups receive vehicle (50% DMSO (JT Baker, Phillipsburg, N.J.)/1× Dulbecco's phosphate saline (GibcoBRL, Grand Island, N.Y.)) or test compound (0.1-10 mg/kg, administered subcutaneously). All rats begin treatment on Day 8 after adjuvant injection.

Statistical analysis is performed using Abacus Concepts SuperANOVA. (Abacus Concepts, Inc., Berkeley, Calif.). All of the parameters of interest are subjected to Analysis of Variance with Duncan's new multiple range post hoc testing between groups. Data are expressed throughout as mean±standard deviation (SD), and differences are deemed significant if $p<0.05$.

The degree of arthritis severity is monitored daily in terms of the following disease indices: Hindpaw erythema, hindpaw swelling, tenderness of the joints, and movements and posture. An integer scale of 0 to 3 is used to quantify the level of erythema (0=normal paw, 1=mild erythema, 2=moderate erythema, 3=severe erythema) and swelling (0=normal paw, 1=mild swelling, 2=moderate swelling, 3=severe swelling of the hind paw). The maximal score per day is 12.

At the end of the study the rats are euthanized with $CO_2$, hindlimbs removed at necropsy and fixed in 10% buffered formalin, and the tarsal joints decalcified and embedded in paraffin. Histologic sections are stained with Hematoxylin and Eosin or Saffranin O—Fast Green stain.

Slides are coded so that the examiner is blinded to the treatment groups. Synovial tissue from tarsal joints is evaluated based on synovial hyperplasia, inflammatory cell infiltration, and pannus formation [Poole and Coombs, International Archives of Allergy & Applied Immunology 54: 97-113 (1977)] as outlined below.

| Category | | Grade |
|---|---|---|
| 1. Synovial lining cells | | |
| | a. No change | 0 |
| | b. Cells enlarged, slightly thickened | 1 |
| | c. Cells enlarged, increase in numbers, moderately thickened. No villus present | 2 |
| | d. Cells enlarged, thickened. Villlus present | 3 |
| 2. Fibroplasia | | |
| | a. No change | 0 |
| | b. Fibroplasia present under lining cells | 1 |
| | c. Small areas of areolar tissue replaced by fibrous tissue | 2 |
| | d. Replacement of areolar tissue by fibrous tissue | 3 |
| 3. Inflammatory cells | | |
| | a. Occasionally seen. scattered throughout selection | 0 |
| | b. Cells present in small numbers in or just under lining cell layer and/or around blood vessels. | 1 |
| | c. Small focal collection of cells may be present | 2 |
| | d. Large numbers of cells present in capsule and in or under lining cell layers. Large foci often seen. | 3 |
| 4. Pannus | | |
| | a. Not detectable | 0 |
| | b. Detectable | 1 |

In addition, articular cartilage and bone is evaluated using Mankin's histological grading system [Mankin, et al., Journal of Bone & Joint Surgery—American Volume 53: 523-37 (1971)] as shown below.

| Category | | Grade |
|---|---|---|
| 1. Structure | | |
| | a. Normal | 0 |
| | b. Surface irregularity | 1 |
| | c. Pannus and surface irregularity | 2 |
| | d. Clefts to transitional zone | 3 |
| | e. Clefts to radial zone | 4 |
| | f. Clefts to calcified zone | 5 |
| | g. Complete disorganization | 6 |
| 2. Cells | | |
| | a. Normal | 0 |
| | b. Diffuse hypercellularity | 1 |
| | c. Cloning | 2 |
| | d. Hypocellularity | 3 |
| 3. Safranin-O staining | | |
| | a. Normal | 0 |
| | b. Slight reduction | 1 |
| | c. Modest reduction | 2 |
| | d. Severe reduction | 3 |
| | e. No dye noted | 4 |
| 4. Tidemark integrity | | |
| | a. Intact | 0 |
| | b. Crossed by blood vessels | 1 |

Evaluation in the HLA-B27 Rat Model of Arthritis

Representative compounds are evaluated in the HLA-B27 rat standard pharmacological test procedure which emulates arthritis in humans. The following briefly describes the procedure used. Male HLA-B27 rats are obtained from Taconic and provided unrestricted access to a food (PMI Lab diet 5001) and water. Rats are dosed subcutaneously once per day with either vehicle (50% DMSO/50% 1× Dulbecco's Phosphate Buffered Saline) or test compound (0.1 to 10 mg/kg) for at least one week. Joint scores and histology are evaluated as described above for the Lewis rat model of adjuvant-induced arthritis.

Evaluation in the Collagen Induced Arthritis Models

Compounds are evaluated in BALB/c mice, 6-8 weeks of age, in which arthritis is induced by monoclonal antibodies raised against type II collagen, plus lipopolysaccharide (LPS). The animals were administered intravenously with a combination of 4 different mAbs totalling 4 mg/mouse on day 0, and followed by intravenous 25 µg of LPS 72 hours later (day 3). From day 3, one hour after LPS application, tested compounds are give orally once daily for 15 days. For each animal, increase in volume of both hind paws is measured using a plethysmometer with water cell (12 mm diameter) on days 0, 5, 7, 10, 14 and 17. Percent inhibition of increase in volume is calculated.

Evaluation in in vivo Models of Carcinogeneisis

The ability of compounds of this invention to treat and inhibit various malignancies or hyperprolific disorders can be evaluated in standard pharmacological test procedures that are readily available in the literature, and include the following two procedures.

Breast cancer. Athymic nu/nu (nude) mice are obtained ovariectomized from Charles River Laboratories (Wilmington, Mass.). One day prior to tumor cell injection, animals are implanted with time-release pellets containing 0.36-1.7 mg 17β-estradiol (60 or 90 day release, Innovative Research of America, Sarasota, Fla.) or a placebo. The pellet is introduced subcutaneously into the intrascapular region using a 10-gauge precision trochar. Subsequently, mice are injected subcutaneously into the breast tissue with either $1\times10^7$ MCF-7 cells or $1\times10^7$ BG-1 cells. The cells are mixed with an equal volume of matrigel, a basement membrane matrix preparation to enhance tumor establishment. Test compounds can be evaluated either by dosing one day after tumor cell implantation (inhibition regimen) or after tumors have reached a certain size (treatment regimen). Compounds are administered either intraperitoneally or orally in a vehicle of 1% tween-80 in saline each day. Tumor size is evaluated every three or seven days.

Colon cancer. The ability to treat or inhibit colon cancer can be evaluated in the test procedure of Smirnoff [Oncology Research 11: 255-64 (1999)].

Evaluation of Neuroprotection in Two in vivo Test Procedures

Transient global ischemia in the Mongolian gerbil. The effect of test compounds on preventing or treating brain injury in response to oxygen deprivation/reperfusion can be measured using the following test procedure.

Female Mongolian gerbils (60-80 g; Charles River Laboratories, Kingston, N.Y.) are housed in the Wyeth-Ayerst animal care facility (AAALAC certified) with a 12-hour light, 12-hour dark photoperiod and free access to tap water and a low-estrogen casein diet (Purina; Richmond, Ind.). After acclimation (3-5 days), gerbils are anesthetized with isoflurane (2-3% mixture with $O_2$), ovariectomized (Day 0). Beginning the following morning (Day 1), gerbils are treated subcutaneously each day with either vehicle (10% ETOH/com oil), 17β-estradiol (1 mg/kg) or an experimental compound (0.1-20 mg/kg). On Day 6, gerbils (n=4-5/group) are anesthetized with isoflurane, the common carotid arteries visualized via a mid-line neck incision and both arteries simultaneously occluded for 5 minutes with non-traumatic micro aneurysm clips. After occlusion, the clips are removed to allow cerebral reperfusion and the neck incision closed with wound clips. All animals are fasted overnight prior to the global ischemia surgery, a step that facilitates consistent ischemic injury. On Day 12, gerbils are exposed to a lethal dose of $CO_2$, and the brains frozen on dry ice and stored at −80° C.

The degree of neuronal protection is evaluated by in situ hybridization analysis of neurogranin mRNA. Briefly, 20 µm coronal cryostat sections are collected on gelatin-coated slides, dried and stored at −80° C. At the time of processing, the desiccated slide boxes are warmed to room temperature, the slides postfixed in 4% paraformaldehyde, treated with acetic anhydride and then delipidated and dehydrated with chloroform and ethanol. Processed section-mounted slides are then hybridized with 200 µl ($6\times10^6$ DPM/slide) of an antisense or sense (control) riboprobe for Neurogranin ($^{35}$S-UTP-labeled NG-241; bases 99-340) in a 50% formamide hybridization mix and incubated overnight at 55° C. in a humidified slide chamber without coverslipping. The following morning, the slides are collected in racks, immersed in 2×SSC (0.3 M NaCl, 0.03 M sodium citrate; pH 7.0)/10 mM DTT, treated with RNase A (20 µg/ml) and washed (2×30 min) at 67° C. in 0.1×SSC to remove nonspecific label. After dehydration, the slides are opposed to BioMax (BMR-1: Kodak) X-ray film overnight.

The level of neurogranin hybridization signal is used to quantitatively assess the degree of neuronal loss in the CA1 region after injury and to evaluate the efficacy of 17β-estradiol and experimental compounds. Neurogranin mRNA is selected for these studies because it is highly expressed in the hippocampal neurons including CA1, but absent in glia and other cell types present in this brain region. Therefore, measurement of the amount of neurogranin mRNA present represents surviving neurons. Relative optical density measurements of neurogranin hybridization signal are obtained from film autoradiograms with a computer based image analysis system (C-Imaging Inc., Pittsburgh, Pa.). The results from 6 sections (40 µm apart) per animal are averaged and statistically evaluated. Numerical values are reported as the mean±SEM. One-way analysis of variance is used to test for differences in the level of neurogranin mRNA and all statements of non-difference in the results section imply that p>0.05.

Middle cerebral artery occlusion in mice. Neuroprotection can be evaluated according to the test procedures described by Dubal [see, Dubal, et al., Proceedings of the National Academy of Sciences of the United States of America 98: 1952-1957 (2001), Dubal, et al., Journal of Neuroscience 19: 6385-6393 (1999)].

Ovulation Inhibition Standard Pharmacological Test Procedure

The test procedure is used to determine whether test compounds can inhibit or change the timing of ovulation. It can also be used to determine the number of oocytes ovulated [Lundeen, et al., J Steroid Biochem Mol Biol 78: 137-143 (2001)].

Transplantation Rejection

To test the ability of the test compounds to prevent transplant rejection. Compounds can be tested in animal models of heart transplantation (Stetson et al. Circulation 104:676-682 (2001) or transplant atherosclerosis (Deitrich et al. Arterioscler. Thromb. Vasc Biol. 20:343-352 (2000). Lou et al., Circulation 94:3355-3361 (1996).

Prevention of Restenosis

The test procedure is used to determine whether test compounds can inhibit vascular smooth muscle cell proliferation after carotid artery injury similar to what occurs after balloon angioplasty. The test compounds can be tested in animal models previously described (Karas et al. Circ Res. 89:534-539 (2001), Cerek et al. Atherosclerosis 131:59-66 (1997).

Treatment of Myocardial Infarction

Test compounds can be tested in animal models of ischemia/reperfusion to determine whether they would inhibit cell death occurring during a myocardial infarction. The compounds can be tested in models described previously (Delyani et al. J Mol & Cell Cardiology 28:1001-1008 (1996), Izumi et al. J Clin Invest. 108:203-213 (2001) & Chandrasekar et al. Circulation 103:2296-2302 (2001)).

Treatment for Myocarditis and Congestive Heart Failure

Test compounds can be tested in models of heart failure to determine whether compounds could be an effective therapy and improve cardiac function. Compounds can be tested in animals as described previously (Yokoseki et al. Circ Res. 89:1-9 (2001), Wallen et al. Hypertension 36:774-779 (2000) & Toshiaki et al. Circulation 104:1094-1103 (2001)).

Treatment for Diabetes

Test compounds can be tested in models of diabetes to determine their effect on reversal of obesity and diet-induced insulin resistance. Compounds can be tested in animal models as previously described (Yuan et al. Science 293:1673-1677 (2001).

Treatment for Asthma

Pulmonary Inflammation Model Sensitize mice with OVA emulsified in alum on days 0 and 14 (ip injection). On days 28 and 29 challenge with an aerosol of OVA for 20 min (1%-5% OVA) and then on Day 30 the animals are sacrificed and harvest BAL and/or lung tissue for analysis of pulmonan, inflammation.

Airway Hyperresponsiveness. This model is similar to that described above however animals are challenged on 3 consecutive days with an aerosol of OVA and airway hyperresponsiveness is measured 48 h after the last challenge BAL can also be taken at this stage if required.

To look more directly at the effects of mast cells in conjunction with ER, may use a passive cutaneous anaphylaxis model in which IgE is injected into the ear and then 24 hours later inject DNP-HSA iv. Measure ear thickness and an early and late phase reaction. Furthermore, fix tissues in K2 and embed in Epoxy resin and cut 1um sections. These can be stained for mast cells and quantitate the degree of mast cell degranulation.

Based on the results obtained in the standard pharmacological test procedures, the compounds of this invention are selective anti-inflammatory compounds described herein useful for the treatment and prevention of chronic inflammatory diseases without stimulating uterine and breast cell proliferation as found with classic estrogens.

Accordingly, the compounds of this invention are useful in treating or inhibiting osteoporosis and in the inhibition of bone demineralization which may result from an imbalance in a individual's formation of new bone tissues and the resorption of older tissues, leading to a net loss of bone. Such bone depletion results in a range of individuals, particularly in post-menopausal women, women who have undergone bilateral oophorectomy, those receiving or who have received extended corticosteroid therapies, those experiencing gonadal dysgenesis, and those suffering from Cushing's syndrome. Special needs for bone, including teeth and oral bone, replacement can also be addressed using these compounds in individuals with bone fractures, defective bone structures, and those receiving bone-related surgeries and/or the implantation of prosthesis. In addition to those problems described above, these compounds can be used in treatment or inhibition for osteoarthritis, hypocalcemia, hypercalcemia, Paget's disease, osteomalacia, osteohalisteresis, multiple myeloma and other forms of cancer having deleterious effects on bone tissues.

The compounds of this invention are also active in the brain and are therefore useful for inhibiting or treating Alzheimer's disease, cognitive decline, decreased libido, senile dementia, neurodegenerative disorders, depression, anxiety, insomnia, schizophrenia, and infertility. The compounds of this invention are also useful in treating or inhibiting benign or malignant abnormal tissue growth including glomerulosclerosis, prostatic hypertrophy, uterine leiomyomas, breast cancer, scleroderma, fibromatosis, endometriosis, endometrial cancer, polycystic ovary syndrome, endometrial polyps, benign breast disease, adenomyosis, ovarian cancer, melanoma, prostate cancer, cancers of the colon, CNS cancers, such as glioma or astioblastomia.

The compounds of this invention are cardioprotective and are antioxidants, and are useful in lowering cholesterol, triglycerides, Lp(a), and LDL levels; inhibiting or treating hypercholesteremia, hyperlipidemia, cardiovascular disease, atherosclerosis, peripheral vascular disease, restenosis, and vasospasm, and inhibiting vascular wall damage from cellular events leading toward immune mediated vascular damage.

The compounds of this invention are also useful in treating disorders associated with inflammation or autoimmune diseases, including inflammatory bowel disease (Crohn's disease, ulcerative colitis, indeterminate colitis), arthritis (rheumatoid arthritis, spondyloarthropathies, osteoarthritis), pleurisy, ischemia/reperfusion injury (e.g. stroke, transplant rejection, myocardial infarction, etc.), asthma, giant cell arteritis, prostatitis, uveitis, psoriasis, multiple sclerosis, systemic lupus erythematosus and sepsis.

The compounds of this invention are also useful in treating or inhibiting ocular disorders including cataracts, uveitis, and macular degeneration and in treating skin conditions such as aging, alopecia, and acne.

The compounds of this invention are also useful in treating or inhibiting metabolic disorders such as type-Hi diabetes, of lipid metabolism, appetite (e.g. anorexia nervosa and bulimia).

Compounds in this invention are also useful in treating or inhibiting bleeding disorders such as hereditary hemorrhagic telangiectasia, dysfunctional uterine bleeding, and combating hemorrhagic shock.

The compounds of this invention are useful in disease states where amenorrhea is advantageous, such as leukemia, endometrial ablations, chronic renal or hepatic disease or coagulation diseases or disorders.

All patents, publications, and other documents cited herein are hereby incorporated by reference in their entirety.

What is claimed:

1. A compound of the formula:

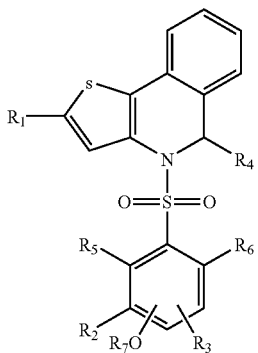

or pharmaceutically acceptable salt thereof, wherein:
$R_1$ is hydrogen, alkyl, halogen, aryl, thienyl, furanyl, or pyrrolyl;
$R_2$, $R_3$, $R_5$, and $R_6$ are, independently, hydrogen, hydroxy, lower alkyl, alkoxy, or halogen;
$R_4$ is alkyl;
$R_7$ is hydrogen, methyl, —(C=O)$R_{16}$, —S(O)$_2R_{17}$, or —S(O)$_2$N($R_{18}$)($R_{19}$);
$R_{16}$ is alkyl;
$R_{17}$ is alkyl, alkenyl or alkynyl; and
$R_{18}$ and $R_{19}$ are, independently, hydrogen, alkyl, alkenyl, or alkynyl.

2. The compound of claim 1 or pharmaceutically acceptable salt thereof wherein $R_5$ and $R_6$ are H.

3. The compound of claim 1 having the formula:

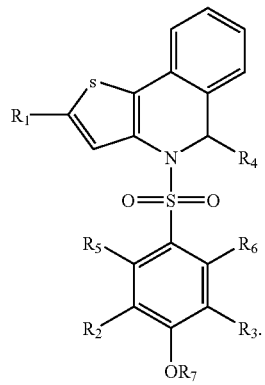

or pharmaceutically acceptable salt thereof.

4. The compound of claim 1 or pharmaceutically acceptable salt thereof wherein $R_1$ is methyl, ethyl, halogen, phenyl, or thienyl.

5. The compound of claim 4 or pharmaceutically acceptable salt thereof wherein $R_1$ is methyl, ethyl, bromo, phenyl, or thienyl.

6. The compound of claim 1 or pharmaceutically acceptable salt thereof wherein $R_2$ is H or Br.

7. The compound of claim 1 or pharmaceutically acceptable salt thereof wherein $R_3$ is H or Br.

8. The compound of claim 1 or pharmaceutically acceptable salt thereof wherein $R_2$ and $R_3$ are each, independently, H or Br.

9. The compound of claim 1 or pharmaceutically acceptable salt thereof wherein $R_4$ is methyl or ethyl.

10. The compound of claim 1 or pharmaceutically acceptable salt thereof wherein $R_7$ is H or methyl.

11. A compound of that is:
   4-[(5-Methylthieno[3,2-c]isoquinolin-4(5H)-yl)sulfonyl]phenol,
   4-[(5-Ethylthieno[3,2-c]isoquinolin-4(5H)-yl)sulfonyl]phenol,
   4-[(2-Bromo-5-methylthieno[3,2-c]isoquinolin-4(5H)yl)sulfonyl]phenol,
   4-{[(5R)-2-bromo-5-methylthieno[3,2-c]isoquinolin-4-(5H)-yl]sulfonyl}phenol,
   4-{[(5S)-2-bromo-5-methylthieno[3,2-c]isoquinolin-4-(5H)-yl]sulfonyl}phenol,
   4-[(2-Bromo-5-ethylthieno[3,2-c]isoquinolin-4(5H)-yl)sulfonyl]phenol,
   4-[(5-Ethyl-2-thien-3-ylthieno[3,2-c]isoquinolin-4(5H)-yl)sulfonyl]phenol,
   4-[(5-Ethyl-2-phenylthieno[3,2-c]isoquinolin-4(5H)-yl)sulfonyl]phenol,
   2-Bromo-4-[(2-bromo-5-methylthieno[3,2-c]isoquinolin-4(5H)-yl)sulfonyl]phenol,
   2,6-Dibromo-4-[(2-bromo-5-methylthieno[3,2-c]isoquinolin-4(5H)-yl)sulfonyl]phenol, or
   4-[(2,5-Diethylthieno[3,2-c]isoquinolin-4(5H)-yl )sulfonyl]phenol, or pharmaceutically acceptable salt thereof.

12. A pharmaceutical composition comprising a compound of claim 1 or pharmaceutically acceptable salt thereof and a pharmaceutical carrier.

* * * * *

SEQUENCE LISTING

```
<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 1
cacacggatg gcgcatact                                                19

<210> SEQ ID NO 2
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 2
ctcgggatgc accatgaag                                                19

<210> SEQ ID NO 3
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 3
cggcactggt ttccctcaca tgct                                          24
```